(12) United States Patent
Smith et al.

(10) Patent No.: US 10,806,331 B2
(45) Date of Patent: Oct. 20, 2020

(54) TORQUE-TRANSMITTING, VARIABLY-FLEXIBLE, LOCKING INSERTION DEVICE AND METHOD FOR OPERATING THE INSERTION DEVICE

(71) Applicant: Syntheon, LLC, Miami, FL (US)

(72) Inventors: Kevin W. Smith, Coral Gables, FL (US); Derek Dee Deville, Coral Gables, FL (US); Korey Kline, Miami, FL (US); Thomas O. Bales, Jr., Miami, FL (US); Matthew A. Palmer, Miami, FL (US); Carlos Rivera, Cooper City, FL (US)

(73) Assignee: Syntheon, LLC, Miami, FL (US)

( * ) Notice: Subject to any disclaimer, the term of this patent is extended or adjusted under 35 U.S.C. 154(b) by 174 days.

(21) Appl. No.: 15/808,489

(22) Filed: Nov. 9, 2017

(65) Prior Publication Data

US 2018/0064311 A1  Mar. 8, 2018

Related U.S. Application Data

(63) Continuation of application No. 11/823,247, filed on Jun. 27, 2007, now Pat. No. 9,814,372.

(51) Int. Cl.
*A61B 1/00* (2006.01)
*A61B 1/005* (2006.01)
(Continued)

(52) U.S. Cl.
CPC ........ *A61B 1/0052* (2013.01); *A61B 1/00154* (2013.01); *A61B 1/31* (2013.01); *A61B 1/0055* (2013.01); *A61B 1/015* (2013.01)

(58) Field of Classification Search
CPC ............................ A61B 1/0051; A61B 1/0052
(Continued)

(56) References Cited

U.S. PATENT DOCUMENTS 3,359,974 A 12/1967 Khalil
3,557,780 A 1/1971 Sato
(Continued)

FOREIGN PATENT DOCUMENTS

WO 2005048814 A2 6/2005
WO 2007093394 A1 8/2007
(Continued)

OTHER PUBLICATIONS

Yarmolenko, et al. NIH Public Access National Institutes of Health, "Thresholds for thermal damage to normal tissues: An update" Int J Hyperthermia. Author manuscript; available in PMC 2013 Mar. 27, 2011 informa UK Ltd.; 27(4): 320-343. doi:10.3109/02656736. 2010.534527.

(Continued)

*Primary Examiner* — Alexandra L Newton
*Assistant Examiner* — Rynae Boler
(74) *Attorney, Agent, or Firm* — Gregory L. Mayback; Rebecca A. Tie; Dickinson Wright PLLC

(57) ABSTRACT

A variably-flexible, locking insertion device includes a hollow body having a proximal end with an entrance for receiving an instrument, a distal end with a tip for protrusion of the instrument, and a handle to be gripped by an operator. A device transitions the hollow body between a relatively flexible condition and a relatively stiff condition. Tendons are disposed within the hollow body for maintaining the hollow body in the relatively flexible and relatively stiff conditions, the tendons being neither in tension nor compression when the hollow body is in the relatively stiff condition.

29 Claims, 25 Drawing Sheets

(51) Int. Cl.
*A61B 1/31* (2006.01)
*A61B 1/015* (2006.01)

(58) Field of Classification Search
USPC .................................. 600/139, 144, 184
See application file for complete search history.

(56) References Cited

U.S. PATENT DOCUMENTS

| | | | |
|---|---|---|---|
| 3,998,216 A | 12/1976 | Hosono | |
| 4,176,662 A | 12/1979 | Frazer | |
| 4,248,234 A | 2/1981 | Assenza et al. | |
| 4,498,473 A | 2/1985 | Gereg | |
| 4,571,240 A | 2/1986 | Samson et al. | |
| 4,575,185 A | 3/1986 | Wentzell | |
| 4,581,390 A | 4/1986 | Flynn | |
| 4,753,223 A | 6/1988 | Bremer | |
| 4,762,118 A | 8/1988 | Lia et al. | |
| 4,784,636 A | 11/1988 | Rydell | |
| 4,815,450 A | 3/1989 | Patel | |
| 4,817,613 A | 4/1989 | Jaraczewski et al. | |
| 4,838,859 A | 6/1989 | Strassmann | |
| 4,848,364 A | 7/1989 | Bosman | |
| 4,890,602 A | 1/1990 | Hake | |
| 4,893,613 A | 1/1990 | Hake | |
| 4,909,787 A | 3/1990 | Danforth | |
| 4,984,581 A | 1/1991 | Stice | |
| 4,998,282 A | 3/1991 | Shishido et al. | |
| 5,069,674 A | 12/1991 | Fearnot et al. | |
| 5,143,085 A | 9/1992 | Wilson | |
| 5,211,633 A | 5/1993 | Stouder, Jr. | |
| 5,222,938 A | 6/1993 | Behl | |
| D337,733 S | 7/1993 | Ewing et al. | |
| 5,240,135 A | 8/1993 | Lepinoy | |
| 5,259,366 A | 11/1993 | Reydel et al. | |
| 5,271,382 A | 12/1993 | Chikama | |
| 5,337,733 A | 8/1994 | Bauerfeind et al. | |
| 5,357,979 A | 10/1994 | Imran | |
| 5,386,817 A | 2/1995 | Jones | |
| 5,423,771 A | 6/1995 | Imran | |
| 5,454,795 A | 10/1995 | Samson | |
| 5,531,685 A | 7/1996 | Hemmer et al. | |
| 5,577,992 A | 11/1996 | Chiba et al. | |
| 5,649,941 A | 7/1997 | Lary | |
| 5,738,100 A | 4/1998 | Yagami et al. | |
| 5,759,151 A | 6/1998 | Sturges | |
| 5,807,237 A | 9/1998 | Tindel | |
| 5,851,203 A | 12/1998 | Van Muiden | |
| 5,873,816 A | 2/1999 | Kagawa et al. | |
| 5,897,536 A | 4/1999 | Nap et al. | |
| 5,931,819 A | 8/1999 | Fariabi | |
| 5,938,623 A | 8/1999 | Quiachon et al. | |
| 6,024,740 A | 2/2000 | Lesh et al. | |
| 6,030,405 A | 2/2000 | Zarbatany et al. | |
| 6,117,068 A | 9/2000 | Gourley et al. | |
| 6,123,084 A | 9/2000 | Jandak et al. | |
| 6,146,339 A | 11/2000 | Biagtan et al. | |
| 6,159,187 A | 12/2000 | Park et al. | |
| 6,196,967 B1 | 3/2001 | Lim et al. | |
| 6,217,565 B1 | 4/2001 | Cohen | |
| 6,309,412 B1 | 10/2001 | Lau et al. | |
| 6,346,077 B1 | 2/2002 | Taylor et al. | |
| 6,375,654 B1 | 4/2002 | McIntyre | |
| 6,387,044 B1 | 5/2002 | Tachibana et al. | |
| 6,451,005 B1 | 9/2002 | Saitou et al. | |
| 6,468,203 B2 | 10/2002 | Belson | |
| 6,478,731 B2 | 11/2002 | Speier et al. | |
| 6,506,150 B1 | 1/2003 | Ouchi | |
| 6,517,477 B1 | 2/2003 | Wendlandt | |
| 6,533,752 B1 | 3/2003 | Waram et al. | |
| 6,562,021 B1 | 5/2003 | Derbin et al. | |
| 6,602,242 B1 | 8/2003 | Fung et al. | |
| 6,610,007 B2 | 8/2003 | Belson et al. | |
| 6,645,223 B2 | 11/2003 | Boyle et al. | |
| 6,800,056 B2 | 10/2004 | Tartaglia et al. | |
| 6,802,809 B2 | 10/2004 | Okada | |
| 6,858,005 B2 | 2/2005 | Ohline et al. | |
| 6,887,235 B2 | 5/2005 | O'Connor et al. | |
| 6,926,669 B1 | 8/2005 | Stewart | |
| 6,942,613 B2 | 9/2005 | Ewers et al. | |
| 6,974,411 B2 | 12/2005 | Belson | |
| 6,984,203 B2 | 1/2006 | Tartaglia et al. | |
| 7,066,880 B2 | 6/2006 | Wendlandt | |
| 7,066,931 B2 | 6/2006 | O'Cconnor et al. | |
| 7,104,951 B2 | 9/2006 | Hasegawa et al. | |
| 7,291,127 B2 | 11/2007 | Eidenschink | |
| 7,435,214 B2 | 10/2008 | Kucklick et al. | |
| 7,465,308 B2 | 12/2008 | Sikora et al. | |
| 7,559,916 B2 | 7/2009 | Smith et al. | |
| 7,736,323 B2 | 6/2010 | Von Weymarn-Scharli | |
| 7,766,896 B2 | 8/2010 | Kornkven Volk et al. | |
| 7,771,411 B2 | 8/2010 | Smith et al. | |
| 7,811,228 B2 | 10/2010 | Adams | |
| 7,914,445 B2 * | 3/2011 | Smith | A61B 1/0055 600/114 |
| 7,988,621 B2 * | 8/2011 | Smith | A61B 1/0055 600/144 |
| 7,998,132 B2 | 8/2011 | Gregorich et al. | |
| 8,092,374 B2 * | 1/2012 | Smith | A61B 1/00078 600/114 |
| 8,100,838 B2 | 1/2012 | Wright et al. | |
| 8,282,677 B2 | 10/2012 | O'Connor et al. | |
| 8,303,570 B2 | 11/2012 | Gregorich et al. | |
| 8,308,722 B2 | 11/2012 | Ormsby et al. | |
| 8,376,960 B2 | 2/2013 | Olson | |
| 8,491,520 B2 | 7/2013 | Smith et al. | |
| 8,523,786 B2 | 9/2013 | Von Weymarn-Scharli | |
| 8,556,804 B2 * | 10/2013 | Smith | A61B 1/31 600/139 |
| 8,814,848 B2 | 8/2014 | Gregorich et al. | |
| 8,821,478 B2 | 9/2014 | Hanson et al. | |
| 8,870,817 B2 | 10/2014 | Kappel et al. | |
| 8,876,772 B2 | 11/2014 | Weber et al. | |
| 8,920,870 B2 | 12/2014 | Weber | |
| 9,155,451 B2 * | 10/2015 | Smith | A61B 1/00078 |
| 9,295,812 B2 | 3/2016 | Wright et al. | |
| 9,333,322 B2 | 5/2016 | Kappel et al. | |
| 9,439,723 B2 | 9/2016 | Beri | |
| 9,526,862 B2 | 12/2016 | Iijima et al. | |
| 9,586,025 B2 | 3/2017 | Salahieh et al. | |
| 9,623,206 B2 | 4/2017 | Melsheimer | |
| 9,629,980 B2 | 4/2017 | O'Day | |
| 9,649,473 B2 | 5/2017 | Gregorich et al. | |
| 9,827,126 B2 | 11/2017 | Losordo et al. | |
| 9,861,782 B2 | 1/2018 | Plassman et al. | |
| 2002/0002323 A1 | 1/2002 | Moriyama | |
| 2002/0082585 A1 | 6/2002 | Carroll et al. | |
| 2002/0177750 A1 | 11/2002 | Pilvisto | |
| 2003/0125764 A1 | 7/2003 | Brady et al. | |
| 2003/0135198 A1 | 7/2003 | Berhow et al. | |
| 2004/0034383 A1 | 2/2004 | Belson | |
| 2004/0044350 A1 | 3/2004 | Martin et al. | |
| 2004/0054322 A1 | 3/2004 | Vargas | |
| 2004/0138529 A1 | 7/2004 | Wiltshire et al. | |
| 2004/0182393 A1 | 9/2004 | MacMillan et al. | |
| 2004/0186350 A1 | 9/2004 | Brenneman et al. | |
| 2005/0075538 A1 | 4/2005 | Banik et al. | |
| 2005/0131279 A1 | 6/2005 | Boulais et al. | |
| 2005/0165275 A1 | 7/2005 | Von Felten et al. | |
| 2006/0025652 A1 | 2/2006 | Vargas | |
| 2006/0069346 A1 | 3/2006 | Smith et al. | |
| 2006/0129130 A1 | 6/2006 | Tal et al. | |
| 2006/0211979 A1 | 9/2006 | Smith et al. | |
| 2007/0088367 A1 | 4/2007 | Von Weymarn-Scharli | |
| 2007/0093689 A1 | 4/2007 | Steinberg | |
| 2007/0179339 A1 | 8/2007 | Gorini et al. | |
| 2007/0208300 A1 | 9/2007 | Pravong et al. | |
| 2007/0215268 A1 | 9/2007 | Pingleton et al. | |
| 2007/0270648 A1 | 11/2007 | Smith et al. | |
| 2007/0272648 A1 | 11/2007 | Keiji et al. | |
| 2008/0009831 A1 | 1/2008 | Griffin | |
| 2008/0091170 A1 | 4/2008 | Vargas et al. | |
| 2008/0097399 A1 | 4/2008 | Sachar et al. | |
| 2008/0228168 A1 | 9/2008 | Mittermeyer et al. | |
| 2008/0269776 A1 | 10/2008 | Justin et al. | |

(56) References Cited

U.S. PATENT DOCUMENTS

| | | |
|---|---|---|
| 2009/0149710 A1 | 6/2009 | Stefanchik et al. |
| 2009/0187163 A1 | 7/2009 | Uihlein |
| 2011/0040282 A1 | 2/2011 | Uihlein |
| 2014/0236120 A1 | 8/2014 | Tsai et al. |
| 2014/0276601 A1 | 9/2014 | Edward |
| 2014/0276642 A1 | 9/2014 | Cully et al. |
| 2015/0272654 A1 | 10/2015 | Esch et al. |
| 2015/0320969 A1 | 11/2015 | Haslinger et al. |
| 2016/0074621 A1 | 3/2016 | Yao et al. |
| 2016/0101261 A1 | 4/2016 | Kugler et al. |
| 2016/0271363 A1 | 9/2016 | Bauer et al. |

FOREIGN PATENT DOCUMENTS

| | | |
|---|---|---|
| WO | 2007131766 A2 | 11/2007 |
| WO | 2010020971 A2 | 2/2010 |
| WO | 2016118671 A1 | 7/2016 |

OTHER PUBLICATIONS

Cordaro, et al.,"Thermodynamic Properties of Molten Nitrate Salts", Sandia National Laboratories: Senior member, Technical Staff, Phd. Livermore, CA, pp. 1-8.

International Search Report an Written Opinion in PCT/US2018/026877 dated Jun. 11, 2018.

Abstract submitted to A/S/G/E, C W Williams, "A Split Overtube for Easier Colonoscopy", Gastrointestial Endoscopt, 1983, p. 188.

International Search Report and Written Opinion of the International Searching Authority dated Aug. 31, 2006, for International Application No. PCT/US2005/034487.

International Search Report for PCT/US/068348 dated Oct. 30, 2008.

International Search Report for PCT/US07/05478 dated Dec. 17, 2007.

International Search Report for PCT/US07/12179 dated Sep. 12, 2008.

International Search Report for PCT/US07/75701 dated Aug. 29, 2008.

International Search Report for PCT/US08/64084 dated Dec. 9, 2008.

\* cited by examiner

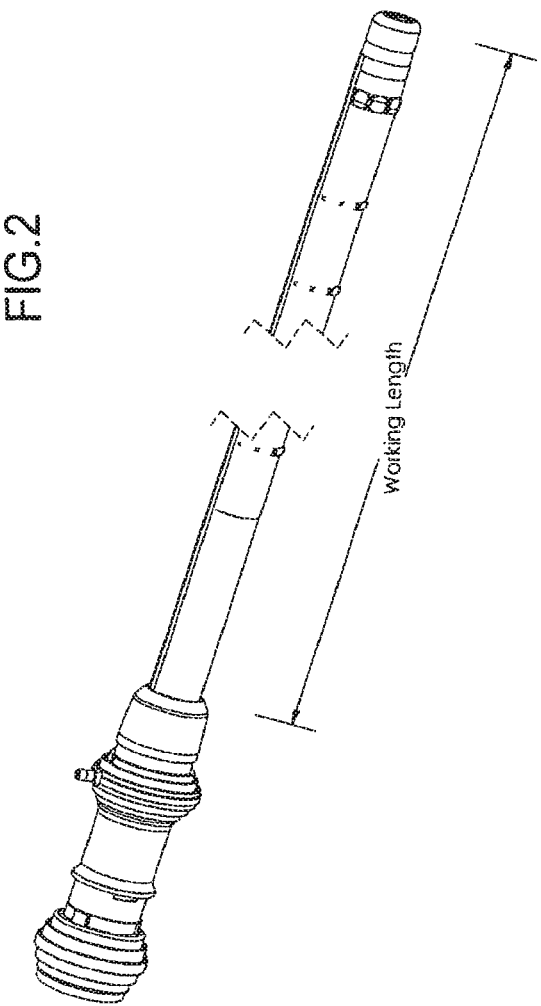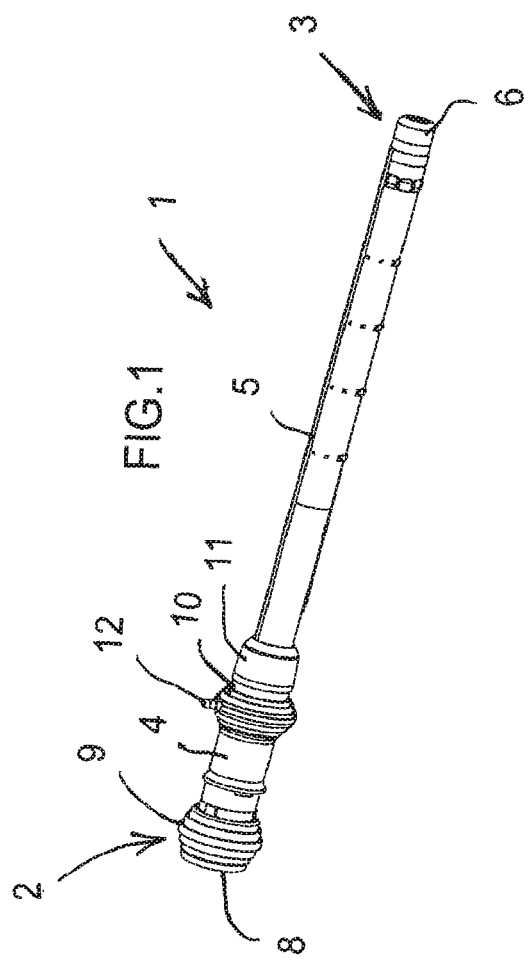

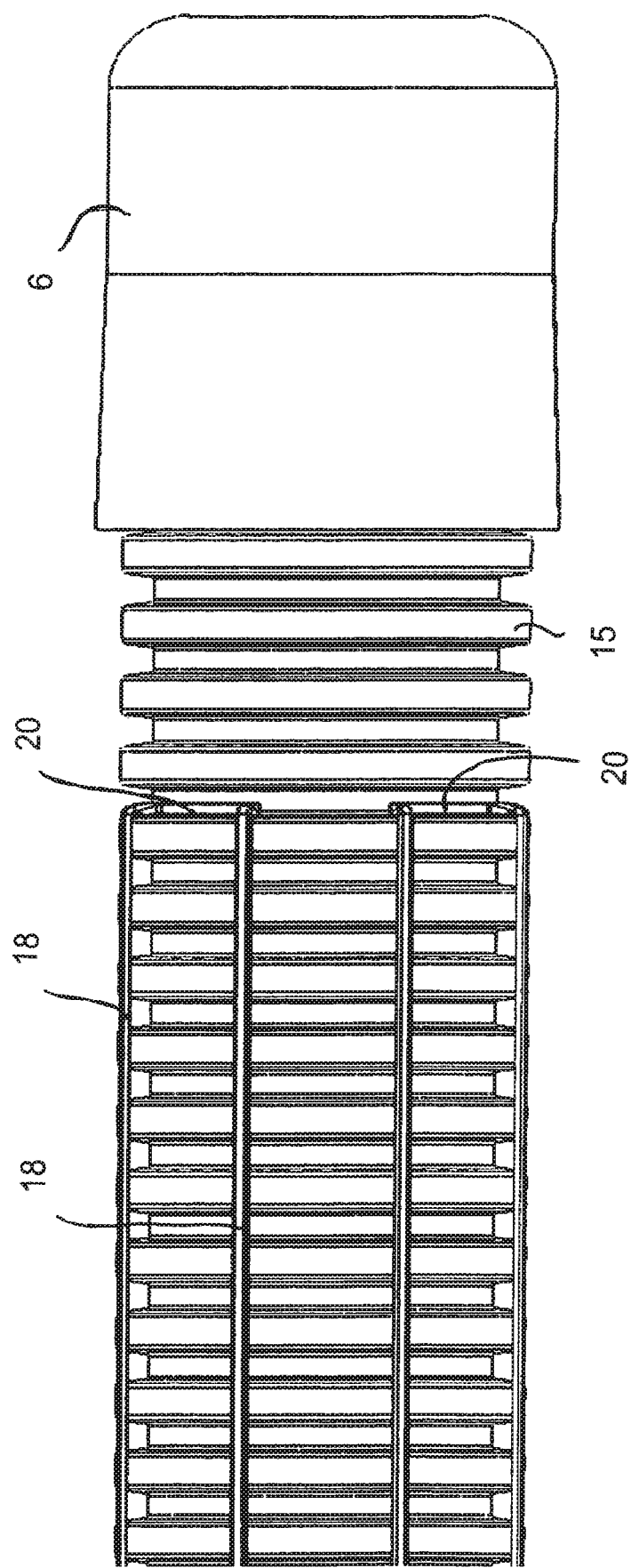

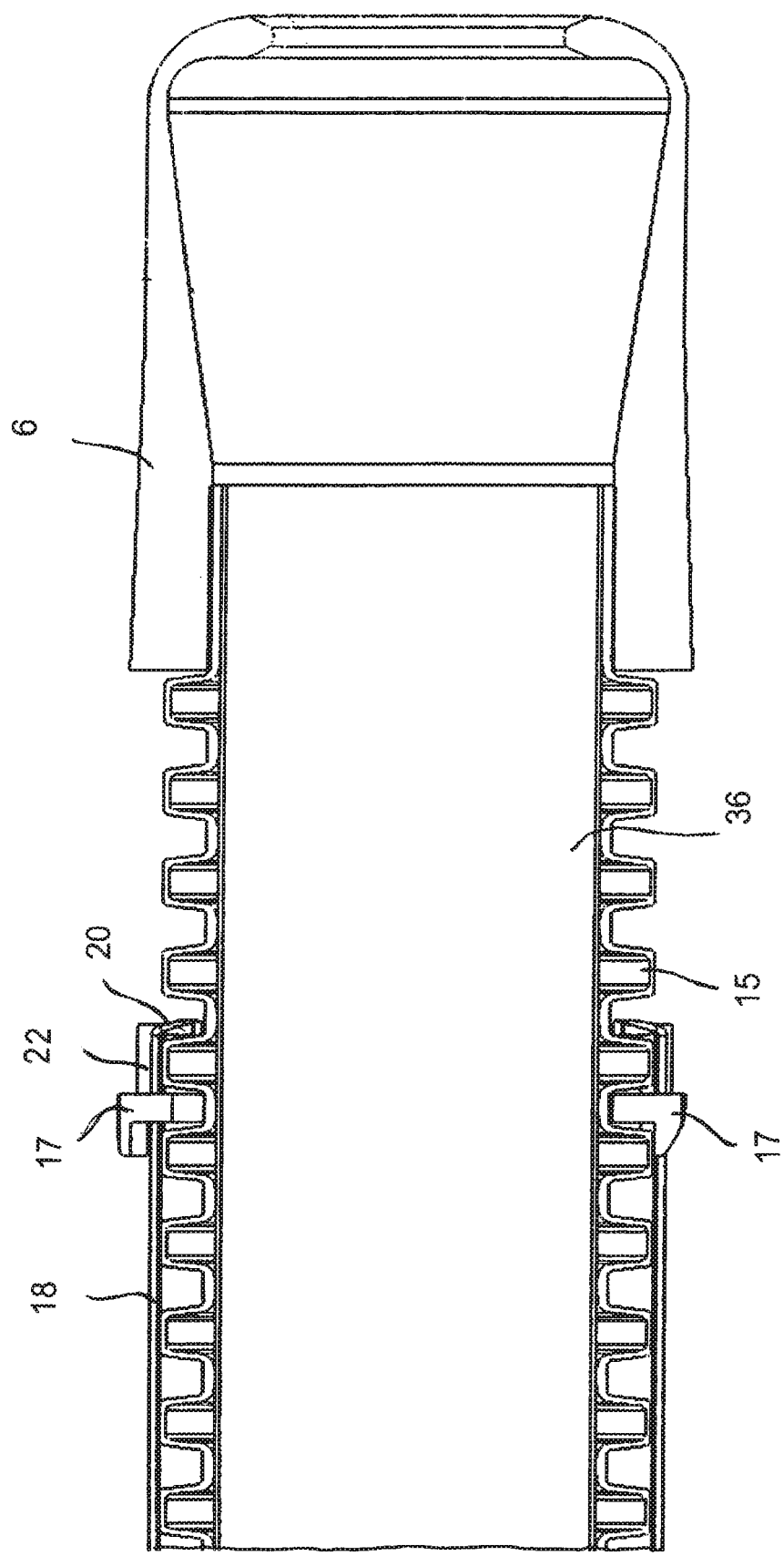

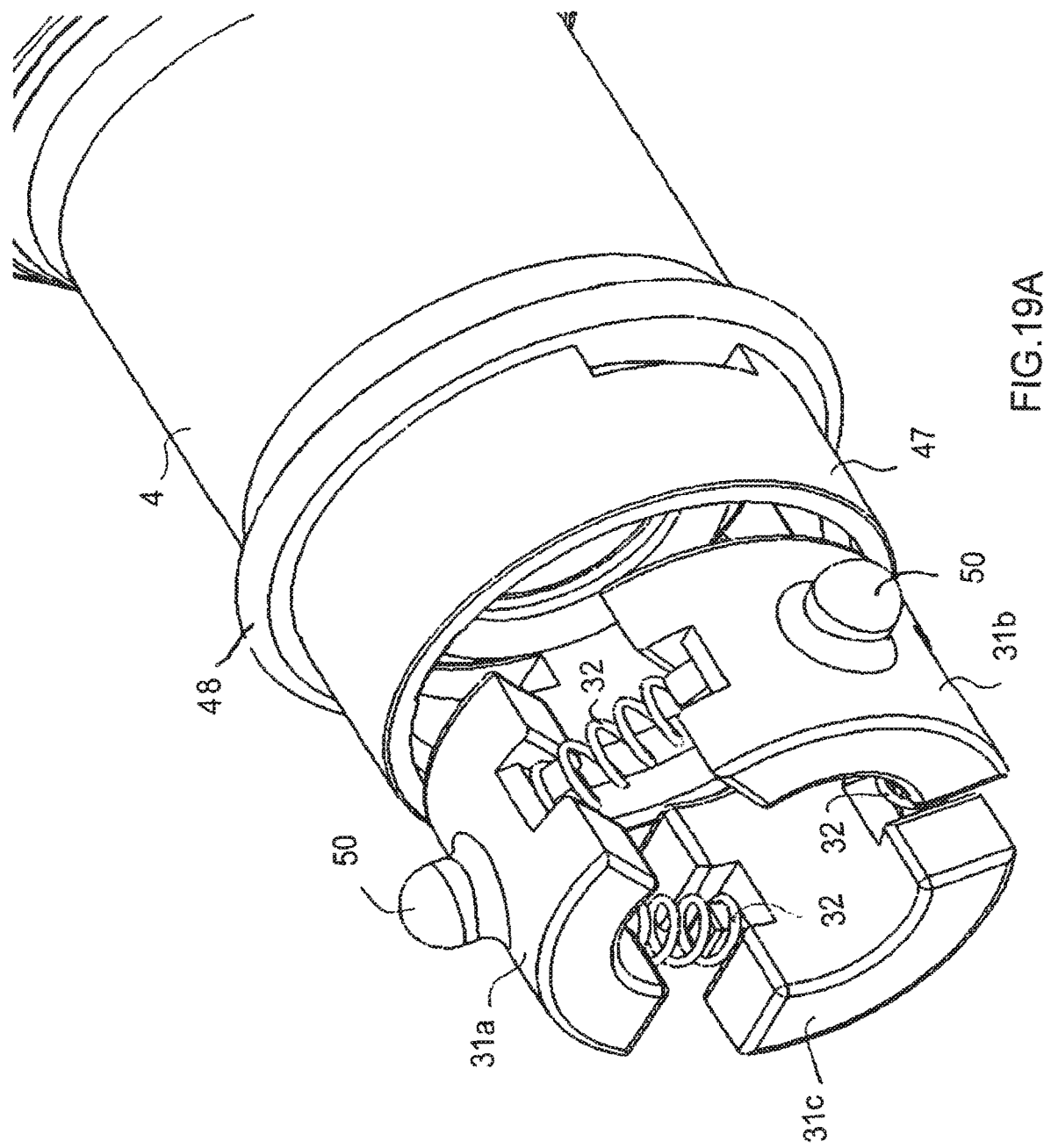

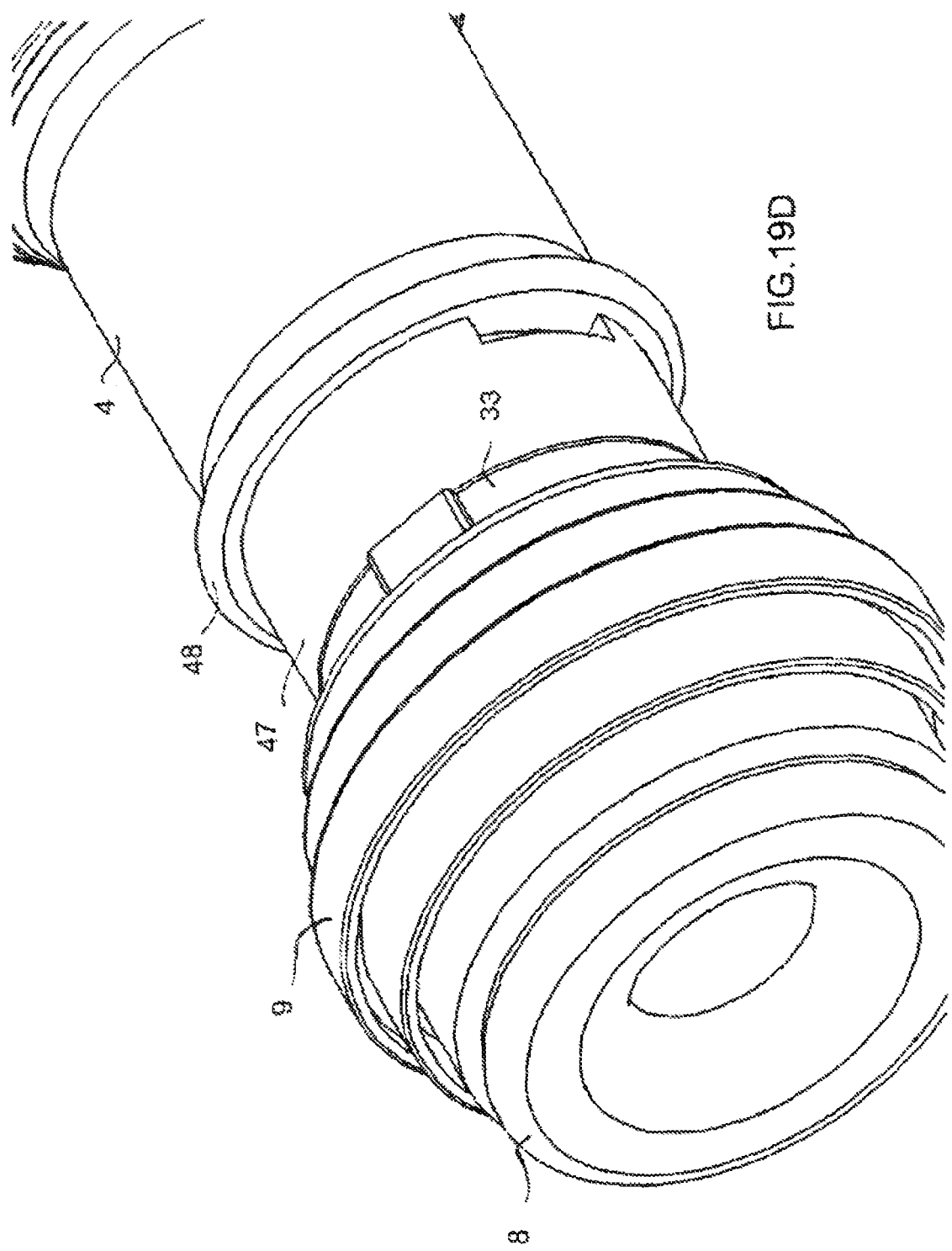

TORQUE-TRANSMITTING, VARIABLY-FLEXIBLE, LOCKING INSERTION DEVICE AND METHOD FOR OPERATING THE INSERTION DEVICE

CROSS-REFERENCE TO RELATED APPLICATIONS

This application is a continuation application of U.S. patent application Ser. No. 11/823,247 filed Jun. 27, 2007, of which priority is claimed under 35 U.S.C. § 120; the prior application is herewith incorporated by reference herein in its entirety.

STATEMENT REGARDING FEDERALLY SPONSORED RESEARCH OR DEVELOPMENT

Not Applicable

FIELD OF THE INVENTION

The invention relates to a torque-transmitting, variably-flexible, locking insertion device. The invention also relates to a method for operating the insertion device.

BACKGROUND OF THE INVENTION

Prior art insertion devices of this general type cannot be connected to an instrument, such as an endoscope or a colonoscope, in such a manner as to be reliable and sufficiently torque-transmitting, while at the same time being easily releasable therefrom and variably flexible. The operator of the device must have the ability to manipulate the instrument when necessary with the insertion device and yet free the instrument easily when necessary.

Devices produced by Spirus Medical, Inc. under the designations Endo-Ease advantage, Endo-Ease discovery and Endo-Ease vista are lightly engaged to and disengaged from a colonoscope and rotate independently thereof. The devices have a spiral at the distal end to follow the lumen of the colon or small bowel when rotated and pushed forward. All three devices have a fixed and predetermined greater flexibility at the distal end and lesser flexibility at the proximal end.

Thus, a need exists to overcome the problems with the prior art systems, designs, and processes as discussed above.

SUMMARY OF THE INVENTION

The disclosure provides a variably-flexible, locking insertion device and a method for operating the insertion device that overcome the hereinafore-mentioned disadvantages of the heretofore-known devices and methods of this general type and which permit an operator of the device to easily and reliably lock the insertion device to and unlock the insertion device from an instrument while varying stiffness.

With the foregoing and other objects in view there is provided, in accordance with the invention, a torque-transmitting, locking insertion device. The insertion device comprises a hollow body having a proximal end with an entrance for receiving an instrument, such as a scope, a distal end with a tip for protrusion of the instrument, and a handle to be gripped by an operator. A device locks the handle to and unlocks the handle from the instrument, which is at least partly disposed within the hollow body. A device, which may be vacuum activated, transitions the hollow body between a relatively flexible condition and a relatively stiff condition.

With the objects of the invention in view, there is also provided a method for operating a torque-transmitting, locking insertion device. The method comprises providing a hollow body having a proximal end with an entrance for receiving an instrument, such as a scope, a distal end with a tip for protrusion of the instrument, and a handle to be gripped by an operator. The instrument is placed at least partly within the hollow body and the handle is locked to and unlocked from the instrument. The hollow body is transitioned between a relatively flexible condition and a relatively stiff condition, such as by vacuum activation.

Thus, through the use of the invention, an operator of the insertion device can not only lock the device to and unlock the device from an instrument, but can also transition the device between relatively flexible and relatively stiff conditions, while applying torque and axial movement to the instrument.

In accordance with another feature of the invention, the locking and unlocking device includes an actuator to be activated by the operator for locking the handle to and unlocking the handle from the instrument. The actuator may be a bobbin to be slid onto the handle by the operator. The locking and unlocking device may also include a clamping plate disposed within the actuator. The clamping plate is moved radially inwardly against the instrument and radially outwardly away from the instrument by activating the actuator. This structure provides a simple and easy to use locking device, which nevertheless delivers reliable locking of an instrument while transmitting torque and advancing axially.

In accordance with a further feature of the invention, the clamping plate includes a plurality of partial-plates, at least one spring biasing the partial-plates radially outwardly and detents integral with the partial-plates. The detents are disposed in recesses in the actuator in a non-actuated condition and slide out of the recesses and push the partial-plates towards the instrument against a force of the at least one spring into an actuated condition. A body tube is disposed partially within the actuator and partially within the handle. The body tube has slots formed therein within which the detents slide between the actuated and non-actuated conditions. The handle has a collar limiting motion of the actuator into the actuated condition. Although the plates, detents and springs are simple elements, they produce reliable locking between the handle and the bobbin.

In accordance with an added feature of the invention, a corrugated tube transmits torque from the proximal end toward the distal end. An inner sleeve disposed within the corrugated tube prevents vacuum leakage and aids in insertion of the instrument. Tendons are disposed along the corrugated tube within the hollow body for maintaining the hollow body in the relatively flexible and relatively stiff conditions.

In accordance with an additional feature of the invention, the hollow body has an outer jacket, the tendons are at least partly disposed between the outer jacket and the corrugated tube, and the transitioning device applies suction between the outer jacket and the corrugated tube for frictionally locking the tendons in place. The corrugated tube provides a certain inherent stiffness, which can be greatly increased by the operator of the insertion device by locking the tendons between the outer jacket and the corrugated tube.

In accordance with yet another feature of the invention, a coupler disposed within the handle defines a vacuum plenum volume therebetween. The handle has a vacuum inlet/outlet hole formed therein communicating with the vacuum plenum volume.

In accordance with yet a further feature of the invention, a sliding valve encircles the handle and has a vacuum inlet/outlet formed therein for communicating with the vacuum connection. The sliding valve slides between a position in which the vacuum inlet/outlet communicates with the vacuum inlet/outlet hole and a position in which the vacuum inlet/outlet is sealed against the vacuum inlet/outlet hole. Thus, the variation in stiffness is provided by simply applying and releasing vacuum when desired by the operator.

In accordance with a concomitant feature of the invention, vertebrae are disposed along the corrugated tube, between corrugation peaks, for guiding the tendons. The vertebrae include at least one last vertebra closest to the distal end. Each two of the tendons form legs of a U-shaped configuration passing through holes in the vertebrae and being interconnected by a crosspiece distally of the last vertebra. There may be two last vertebrae between which the crosspiece is fixed. The tendons may vary in number along the hollow body for providing zones of varying stiffness. The tendons float when the hollow body is in the relatively flexible condition. The tendons are not in tension or compression when the hollow body is in the relatively stiff condition. The tendons are not under tension in both the relatively flexible and relatively stiff conditions. The combination of the vertebrae and the tendons provide inherent stiffness to the degree desired, while permitting added stiffness to be attained by the transitioning device.

With the foregoing and other objects in view, there is provided, a variably-flexible, locking insertion device, comprising a hollow body having a proximal end with an entrance for receiving an instrument, a distal end with a tip for protrusion of the instrument, and a handle to be gripped by an operator, a device for transitioning the hollow body between a relatively flexible condition and a relatively stiff condition, and tendons disposed within the hollow body for maintaining the hollow body in the relatively flexible and relatively stiff conditions, the tendons being neither in tension nor compression when the hollow body is in the relatively stiff condition.

With the objects in view, there is also provided a variably-flexible, locking insertion device comprising a hollow body having a proximal end with an entrance for receiving an instrument, a distal end with a tip for protrusion of the instrument, and a handle to be gripped by an operator, a vacuum-actuated transitioning device surrounding at least a portion of the hollow to change the hollow body between a relatively flexible condition and a relatively stiff condition, and tendons disposed within the hollow body for maintaining the hollow body in the relatively flexible and relatively stiff conditions, the tendons being neither in tension nor compression when the hollow body is in the relatively stiff condition.

With the objects in view, there is also provided a variably-flexible, locking insertion device comprising a hollow body having a proximal end with an entrance for receiving an instrument, a distal end with a tip for protrusion of the instrument, and a handle to be gripped by an operator, a vacuum-actuated device transitioning the hollow body between a relatively flexible condition and a relatively stiff condition and comprising an outer jacket surrounding the hollow body and defining a vacuum plenum volume between the hollow body and the outer jacket and a vacuum inlet/outlet hole fluidically connected to the vacuum plenum volume and, when a vacuum is provided at the vacuum inlet/outlet hole, the vacuum plenum volume is compressed by ambient pressure to place the vacuum-actuated device into the relatively stiff condition, and tendons at least partly disposed between the outer jacket and the hollow body for maintaining the hollow body in the relatively flexible and relatively stiff conditions, the tendons being neither in tension nor compression when the hollow body is in the relatively stiff condition.

With the objects in view, there is also provided a variably-flexible, locking insertion device comprising a hollow body having a proximal end with an entrance for receiving an instrument, a distal end with a tip for protrusion of the instrument, and a handle to be gripped by an operator, a device for transitioning the hollow body between a relatively flexible condition and a relatively stiff condition, and a network of longitudinal support beams disposed within the hollow body for maintaining the hollow body in the relatively flexible and relatively stiff conditions, the support beams being neither in tension nor compression when the hollow body is in the relatively stiff condition.

In accordance with another feature, the transitioning device is vacuum activated.

In accordance with a further feature, the transitioning device includes a vacuum connection at which a vacuum is applied.

In accordance with an added feature, there is provided a corrugated tube around the hollow body for transmitting torque from the proximal end toward the distal end and an inner sleeve disposed within the corrugated tube for preventing vacuum leakage and aiding in insertion of the instrument.

In accordance with an additional feature, the tendons are disposed along the corrugated tube along the hollow body to maintain the hollow body in the relatively flexible and relatively stiff conditions.

In accordance with yet another feature, there is provided an outer jacket around the hollow body, the tendons are at least partly disposed between the outer jacket and the corrugated tube, and the transitioning device applies suction between the outer jacket and the corrugated tube to frictionally lock the tendons in place. In accordance with yet a further feature, the In accordance with yet an added feature, there are provided tendon guiding devices disposed circumferentially about the hollow body and shaped to maintain the tendons in a longitudinal orientation with respect to the hollow body.

In accordance with yet an additional feature, the tendon guiding devices are vertebrae disposed along the hollow body and having holes guiding the tendons.

In accordance with again another feature, the vertebrae include at least one last vertebra closest to the distal end and each two of the tendons form legs of a U-shaped configuration passing through the holes and are interconnected by a crosspiece distally of the at least one last vertebra.

In accordance with again a further feature, the vacuum-actuated device applies suction between the outer jacket and the corrugated tube to frictionally lock the tendons in place.

In accordance with again an added feature, each of the longitudinal support beams has a proximal end and a distal end and is linear from the proximal end to the distal end.

In accordance with again an additional feature, the support beams are disposed along the corrugated tube along the hollow body to maintain the hollow body in the relatively flexible and relatively stiff conditions.

In accordance with still another feature, there is provided an outer jacket around the hollow body, the support beams are at least partly disposed between the outer jacket and the corrugated tube, and the transitioning device applies suction between the outer jacket and the corrugated tube to frictionally lock the support beams in place.

In accordance with still a further feature, there are provided beam guiding devices disposed circumferentially about the hollow body and shaped to maintain the support beams in a longitudinal orientation with respect to the hollow body.

In accordance with still an added feature, the beam guiding devices are vertebrae disposed along the corrugated tube and having holes guiding the support beams.

In accordance with a concomitant feature, the vertebrae include at least one last vertebra closest to the distal end and each two of the support beams form legs of a U-shaped configuration passing through the holes and are interconnected by a crosspiece distally of the at least one last vertebra.

Other features which are considered as characteristic for the invention are set forth in the appended claims.

Although the systems, apparatuses, and methods are illustrated and described herein as embodied in a variably-flexible, locking insertion device and a method for operating the insertion device, it is, nevertheless, not intended to be limited to the details shown because various modifications and structural changes may be made therein without departing from the spirit of the invention and within the scope and range of equivalents of the claims. Additionally, well-known elements of exemplary embodiments will not be described in detail or will be omitted so as not to obscure the relevant details of the systems, apparatuses, and methods.

Additional advantages and other features characteristic of the systems, apparatuses, and methods will be set forth in the detailed description that follows and may be apparent from the detailed description or may be learned by practice of exemplary embodiments. Still other advantages of the systems, apparatuses, and methods may be realized by any of the instrumentalities, methods, or combinations particularly pointed out in the claims.

Other features that are considered as characteristic for the systems, apparatuses, and methods are set forth in the appended claims. As required, detailed embodiments of the systems, apparatuses, and methods are disclosed herein; however, it is to be understood that the disclosed embodiments are merely exemplary of the systems, apparatuses, and methods, which can be embodied in various forms. Therefore, specific structural and functional details disclosed herein are not to be interpreted as limiting, but merely as a basis for the claims and as a representative basis for teaching one of ordinary skill in the art to variously employ the systems, apparatuses, and methods in virtually any appropriately detailed structure. Further, the terms and phrases used herein are not intended to be limiting; but rather, to provide an understandable description of the systems, apparatuses, and methods. While the specification concludes with claims defining the systems, apparatuses, and methods of the invention that are regarded as novel, it is believed that the systems, apparatuses, and methods will be better understood from a consideration of the following description in conjunction with the drawing figures, in which like reference numerals are carried forward.

BRIEF DESCRIPTION OF THE DRAWINGS

The accompanying figures, where like reference numerals refer to identical or functionally similar elements throughout the separate views, which are not true to scale, and which, together with the detailed description below, are incorporated in and form part of the specification, serve to illustrate further various embodiments and to explain various principles and advantages all in accordance with the systems, apparatuses, and methods. Advantages of embodiments of the systems, apparatuses, and methods will be apparent from the following detailed description of the exemplary embodiments thereof, which description should be considered in conjunction with the accompanying drawings in which:

FIG. 1 is a diagrammatic, perspective view of a torque-transmitting, variably-flexible, locking insertion device according to the invention;

FIG. 2 is a perspective view similar to FIG. 1, showing a working length of the insertion device;

FIGS. 9A and 9B are even further enlarged, fragmentary, elevational views of a distal end of the insertion device in which a locking ring is respectively shown and omitted for clarity and in which the outer jacket has been removed;

FIGS. 11A, 11B and 11C are fragmentary, longitudinal-sectional views of the distal end of the insertion device with the outer jacket removed and respectively showing two locking rings, one locking ring and no locking ring;

FIGS. 19A, 19B, 19C and 19D are enlarged, fragmentary, perspective views of the proximal end of the insertion device respectively showing a handle with a clamping plate, a body tube slid over the clamping plate, an end cap at the proximal end and a bobbin distally of the end cap.

DETAILED DESCRIPTION OF THE EMBODIMENTS

Figure 3:
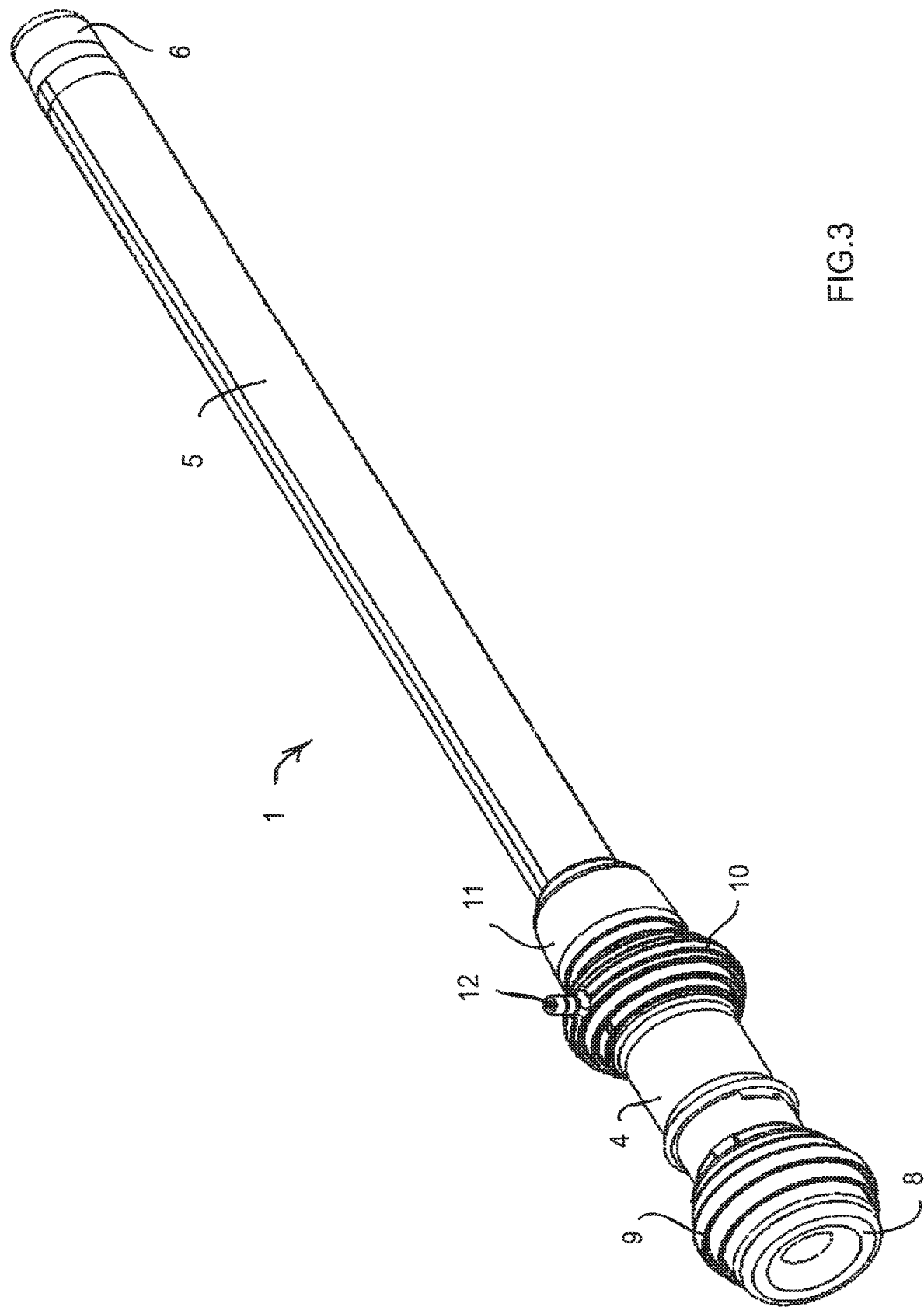
FIG. 3 is an enlarged, perspective view of the insertion device, showing details of a proximal end.

As required, detailed embodiments of the systems, apparatuses, and methods are disclosed herein; however, it is to be understood that the disclosed embodiments are merely exemplary of the systems, apparatuses, and methods, which can be embodied in various forms. Therefore, specific structural and functional details disclosed herein are not to be interpreted as limiting, but merely as a basis for the claims and as a representative basis for teaching one skilled in the art to variously employ the systems, apparatuses, and methods in virtually any appropriately detailed structure. Further, the terms and phrases used herein are not intended to be limiting; but rather, to provide an understandable description of the systems, apparatuses, and methods. While the specification concludes with claims defining the features of the systems, apparatuses, and methods that are regarded as novel, it is believed that the systems, apparatuses, and methods will be better understood from a consideration of the following description in conjunction with the drawing figures, in which like reference numerals are carried forward.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Alternate embodiments may be devised without departing from the spirit or the scope of the invention. Additionally, well-known elements of exemplary embodiments of the systems, apparatuses, and methods will not be described in detail or will be omitted so as not to obscure the relevant details of the systems, apparatuses, and methods.

Before the systems, apparatuses, and methods are disclosed and described, it is to be understood that the terminology used herein is for the purpose of describing particular embodiments only and is not intended to be limiting. The terms "comprises," "comprising," or any other variation thereof are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element. The terms "including" and/or "having," as used herein, are defined as comprising (i.e., open language). The terms "a" or "an", as used herein, are defined as one or more than one. The term "plurality," as used herein, is defined as two or more than two. The term "another," as used herein, is defined as at least a second or more. The description may use the terms "embodiment" or "embodiments," which may each refer to one or more of the same or different embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact (e.g., directly coupled). However, "coupled" may also mean that two or more elements are not in direct contact with each other, but yet still cooperate or interact with each other (e.g., indirectly coupled).

For the purposes of the description, a phrase in the form "A/B" or in the form "A and/or B" or in the form "at least one of A and B" means (A), (B), or (A and B), where A and B are variables indicating a particular object or attribute. When used, this phrase is intended to and is hereby defined as a choice of A or B or both A and B, which is similar to the phrase "and/or". Where more than two variables are present in such a phrase, this phrase is hereby defined as including only one of the variables, any one of the variables, any combination of any of the variables, and all of the variables, for example, a phrase in the form "at least one of A, B, and C" means (A), (B), (C), (A and B), (A and C), (B and C), or (A, B and C).

Relational terms such as first and second, top and bottom, and the like may be used solely to distinguish one entity or action from another entity or action without necessarily requiring or implying any actual such relationship or order between such entities or actions. The description may use perspective-based descriptions such as up/down, back/front, top/bottom, and proximal/distal. Such descriptions are merely used to facilitate the discussion and are not intended to restrict the application of disclosed embodiments. Various operations may be described as multiple discrete operations in turn, in a manner that may be helpful in understanding embodiments; however, the order of description should not be construed to imply that these operations are order dependent.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. As used herein, the terms "substantial" and "substantially" means, when comparing various parts to one another, that the parts being compared are equal to or are so close enough in dimension that one skill in the art would consider the same. Substantial and substantially, as used herein, are not limited to a single dimension and specifically include a range of values for those parts being compared. The range of values, both above and below (e.g., "+/−" or greater/lesser or larger/smaller), includes a variance that one skilled in the art would know to be a reasonable tolerance for the parts mentioned.

Herein various embodiments of the systems, apparatuses, and methods are described. In many of the different embodiments, features are similar. Therefore, to avoid redundancy, repetitive description of these similar features may not be made in some circumstances. It shall be understood, however, that description of a first-appearing feature applies to the later described similar feature and each respective description, therefore, is to be incorporated therein without such repetition.

Referring now to the figures of the drawings in detail and first, particularly, to FIGS. 1 and 2 thereof, there is seen a torque-transmitting, variably-flexible, locking insertion device 1 according to the invention having a working length. The insertion device 1 has a hollow body with a proximal end 2 for manipulation by an operator and for receiving an instrument 40 such as an endoscope or a colonoscope, shown in FIG. 13. The insertion device 1 also has a distal end 3 for insertion into a patient and for protrusion of the instrument. A handle 4 of the hollow body for control by the operator is disposed at the proximal end 2. An outer jacket or sleeve 5 of the hollow body extends to a tip 6, which may be formed of rubber, at the distal end 3. As will be explained below, the handle 4 has an end cap 8, an actuator or bobbin 9 for locking an instrument, a sliding valve or slider 10 and a forward stop 11. The handle 4 also has a vacuum connection or nipple 12 for controlling stiffness of the device, as will be explained below as well. A corrugated tube 15 in the region of the distal tip 6, which is illustrated in other figures, extends to the coupler 35.

Figure 4:
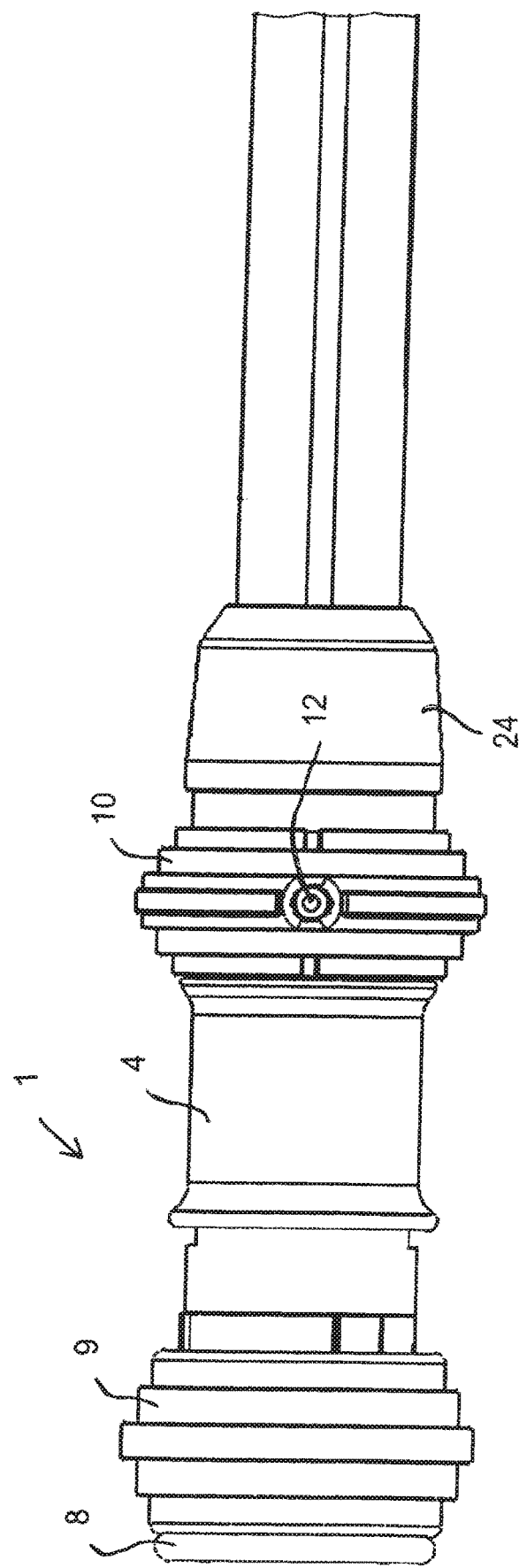
FIG. 4 is a fragmentary, further enlarged, top-plan view of the proximal end of the insertion device.
Figure 5:
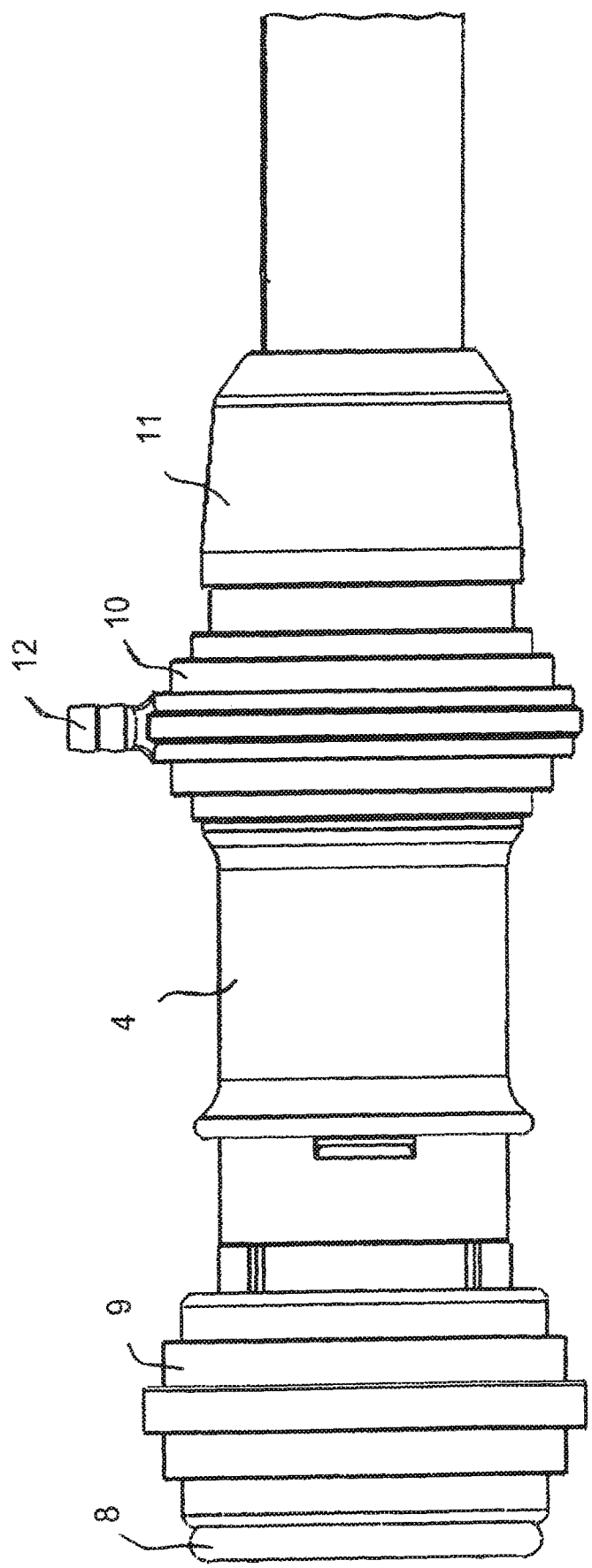
FIG. 5 is an even further enlarged, fragmentary, side-elevational view of the proximal end of the insertion device.

FIGS. 3, 4 and 5 are enlarged perspective, top and side views showing the insertion device 1, from which the end cap 8, the actuator or bobbin 9, the handle 4, the sliding valve or slider 10 with the nipple 12, the forward stop 1 and the strain relief retainer 7, can be seen more clearly. FIG. 3 also shows the outer jacket 5 and the distal tip 6.

Figure 6:
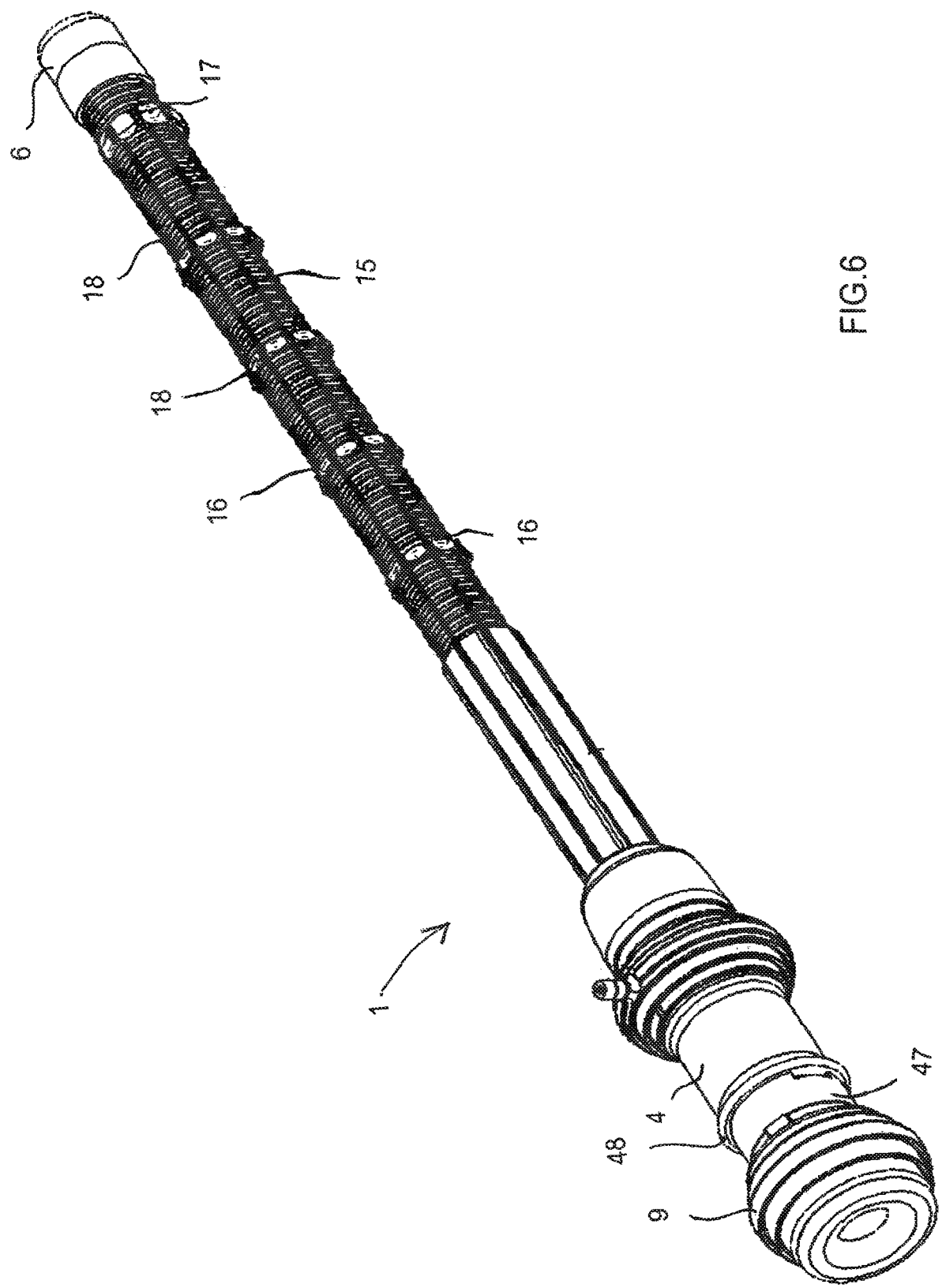
FIG. 6 is a perspective view of the insertion device with an outer jacket removed.
Figure 7:
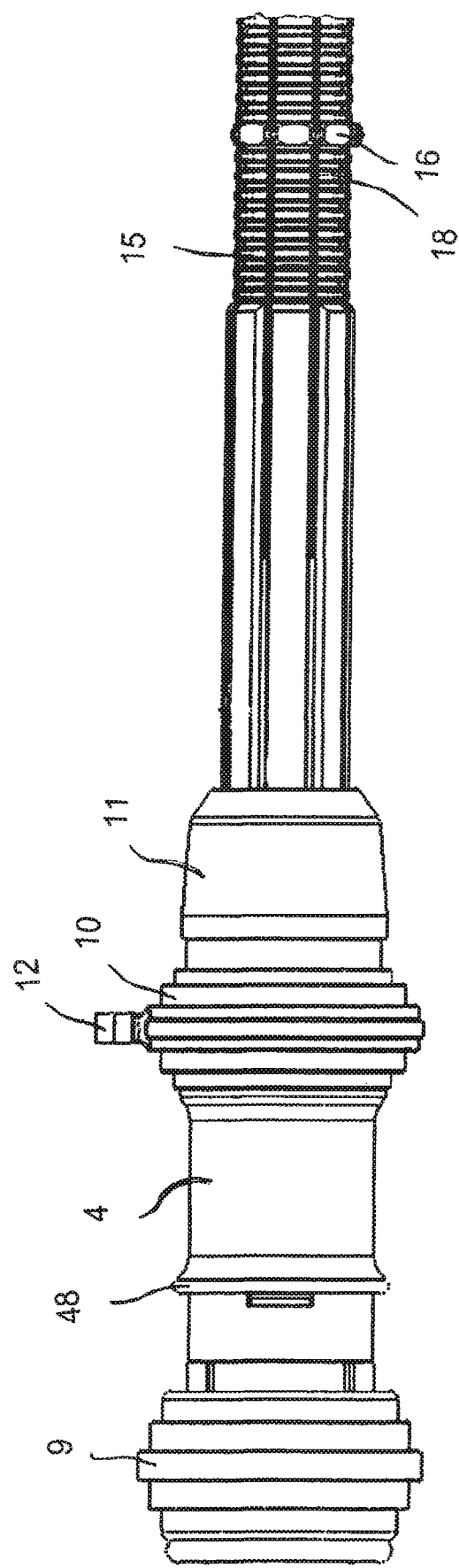
FIG. 7 is a fragmentary, enlarged, side-elevational view of the proximal end and part of the working length of the insertion device with the outer jacket removed.
Figure 8:
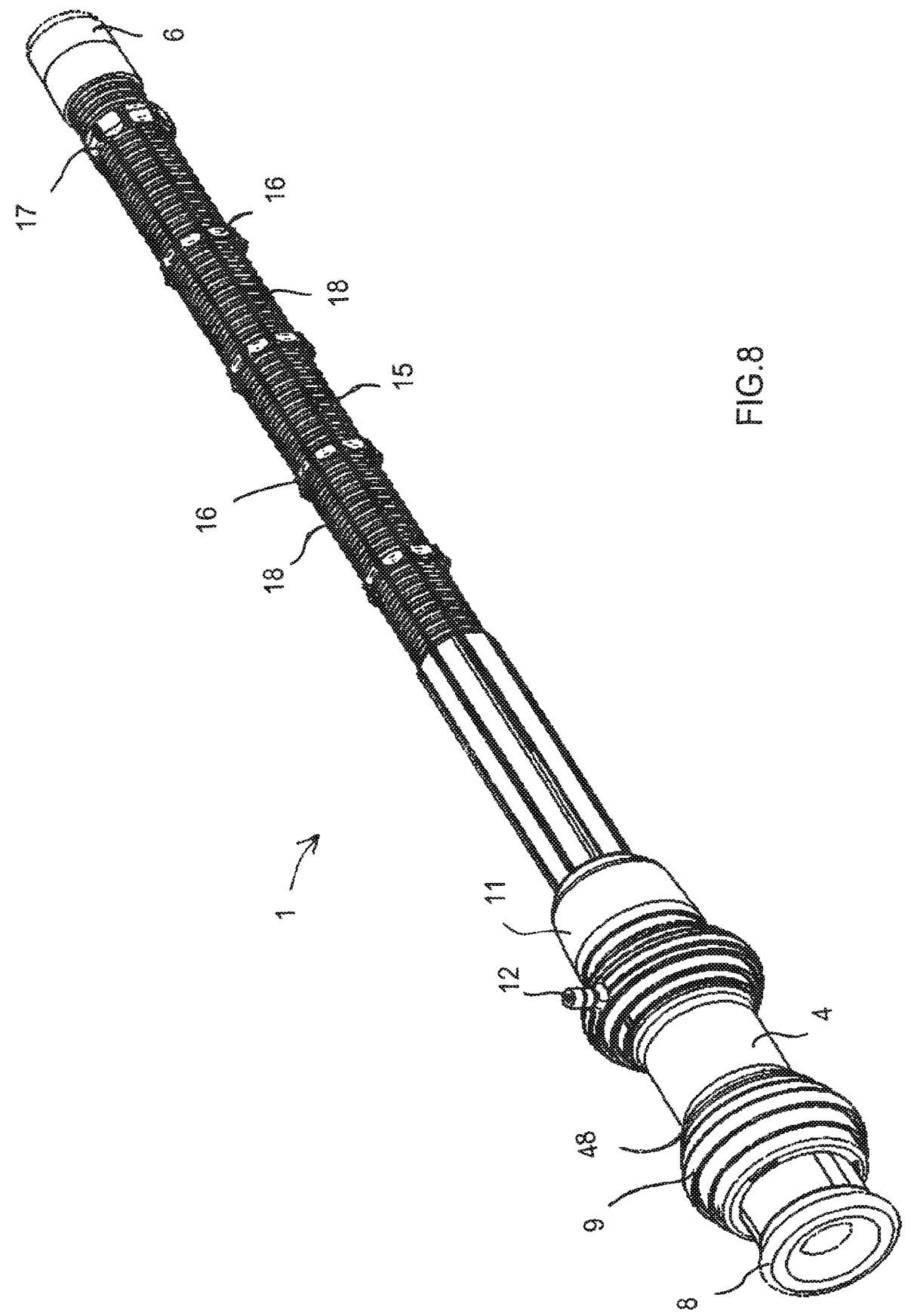
FIG. 8 is a view similar to FIG. 6, of the insertion device with a lock in an actuated condition.
Figure 9A:
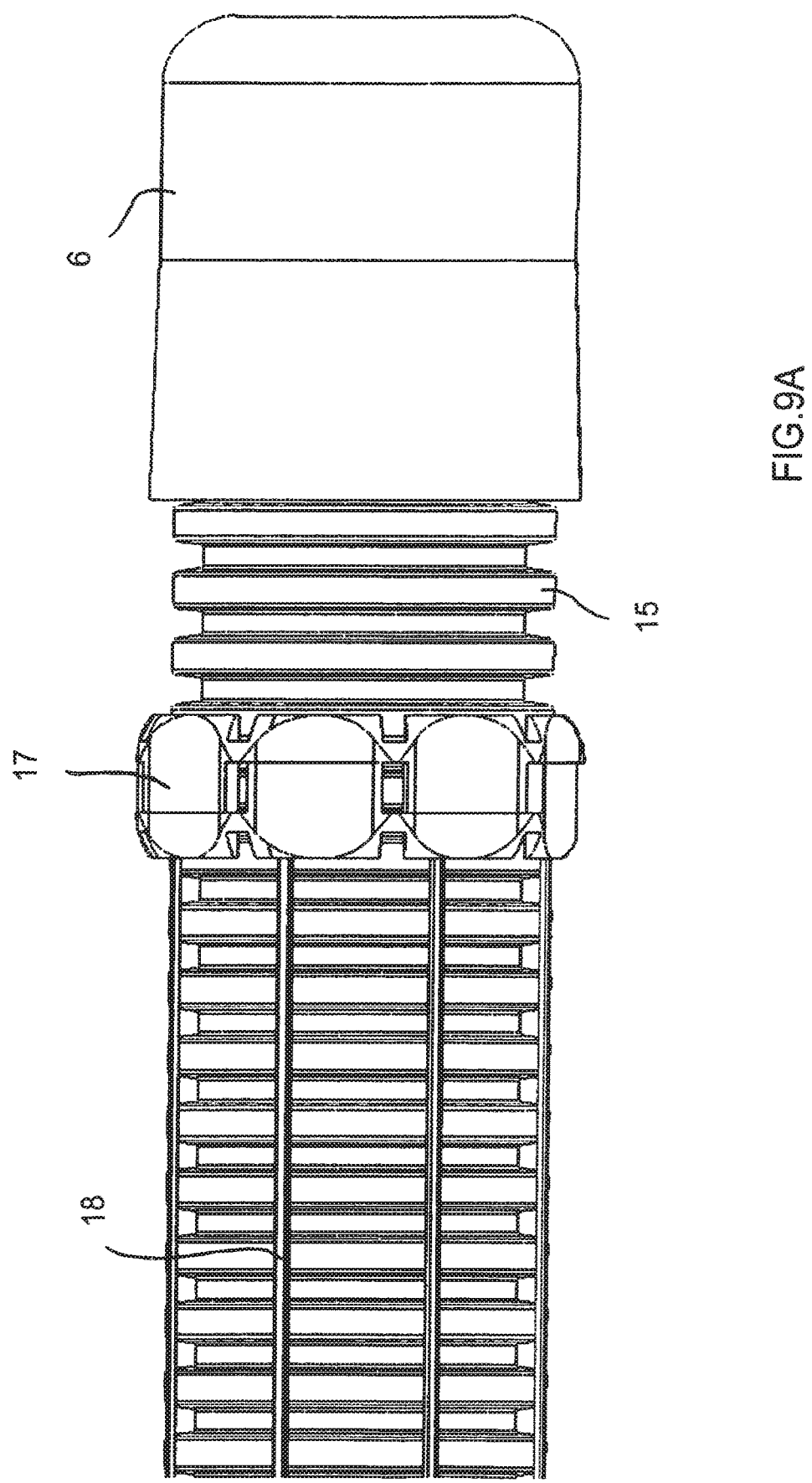
Figure 10A:
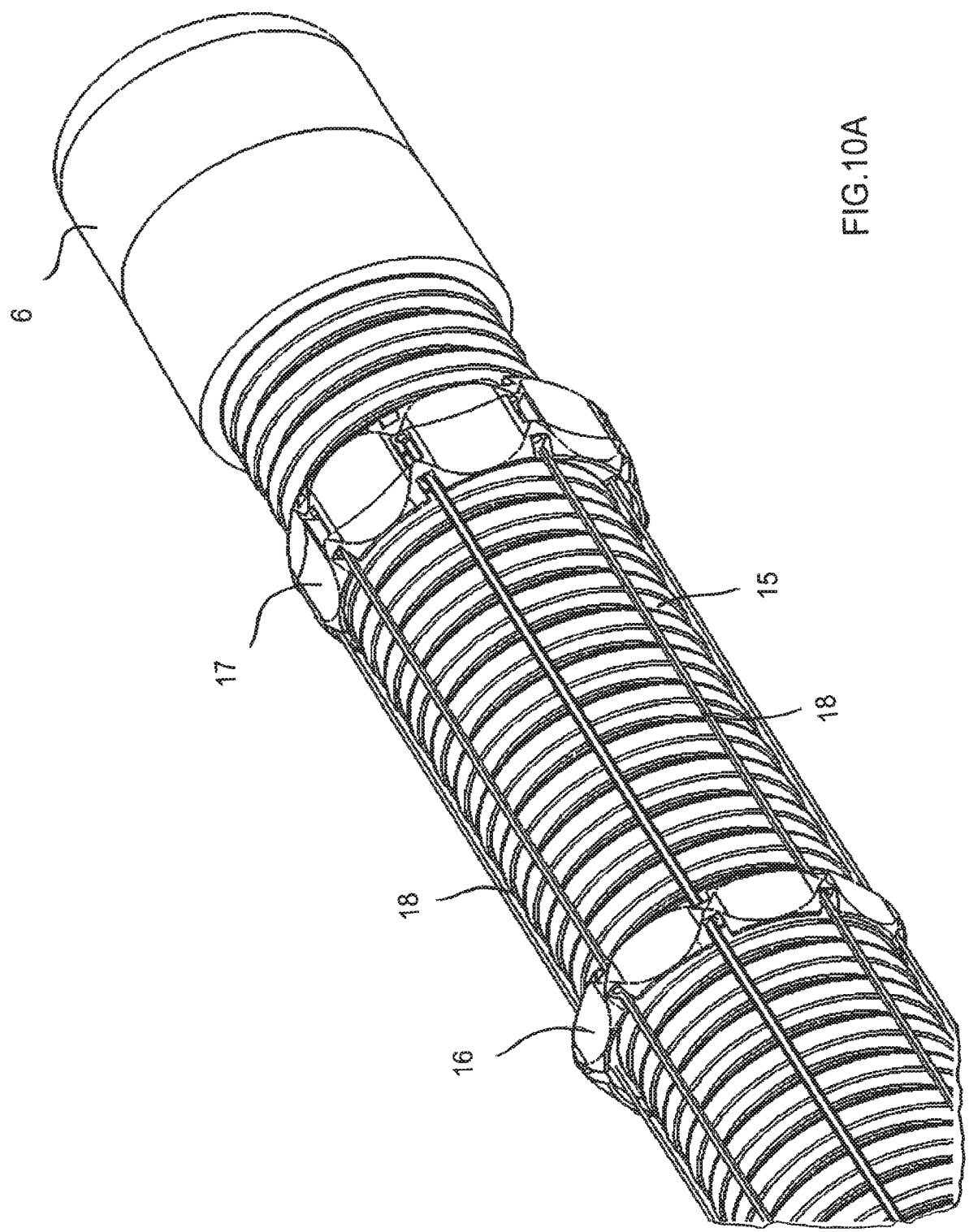
FIGS. 10A and 10B are fragmentary, perspective views of the distal end of the insertion device in which the locking ring is respectively shown and omitted for clarity and in which the outer jacket has been removed.
Figure 10B:
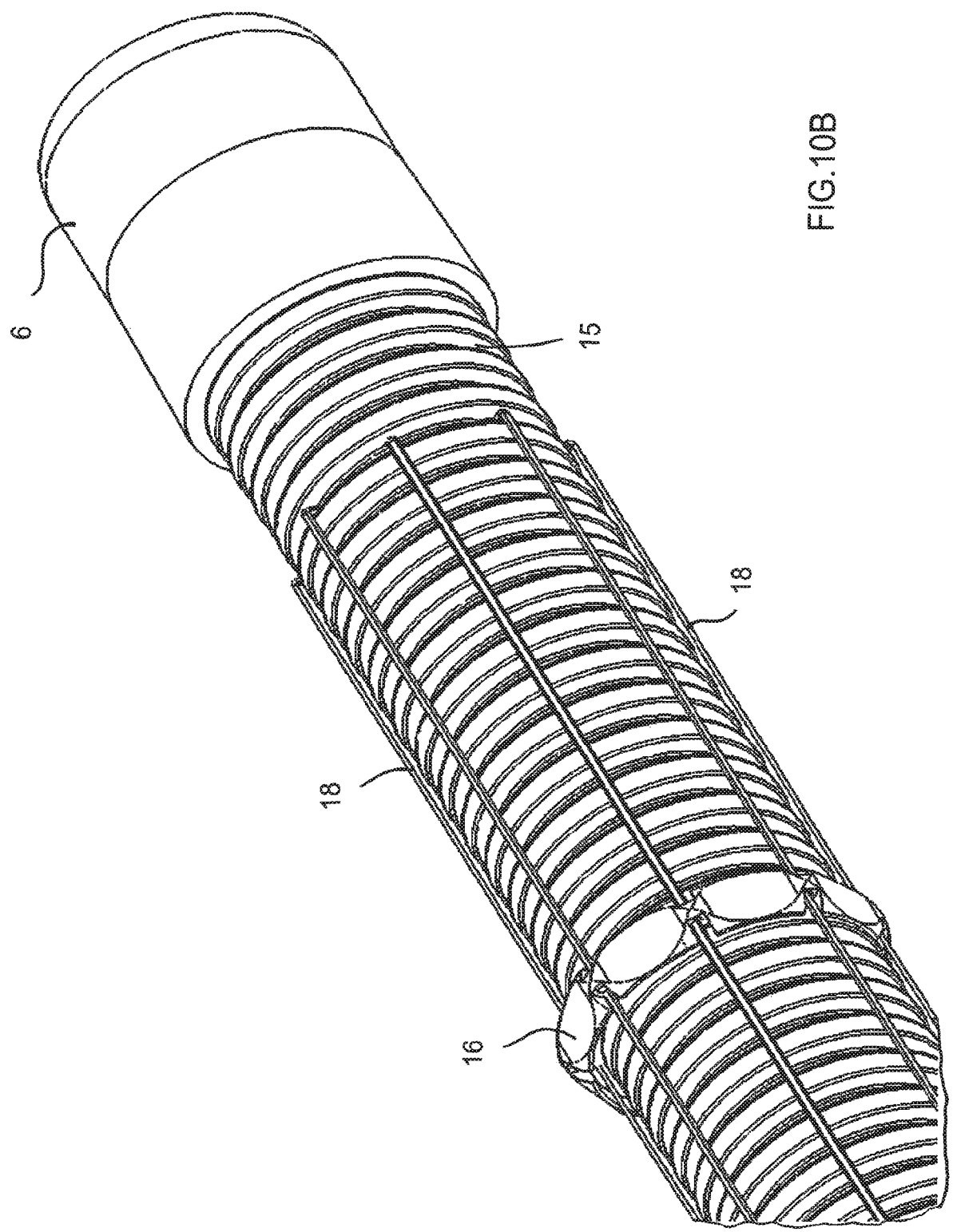
Figure 11A:
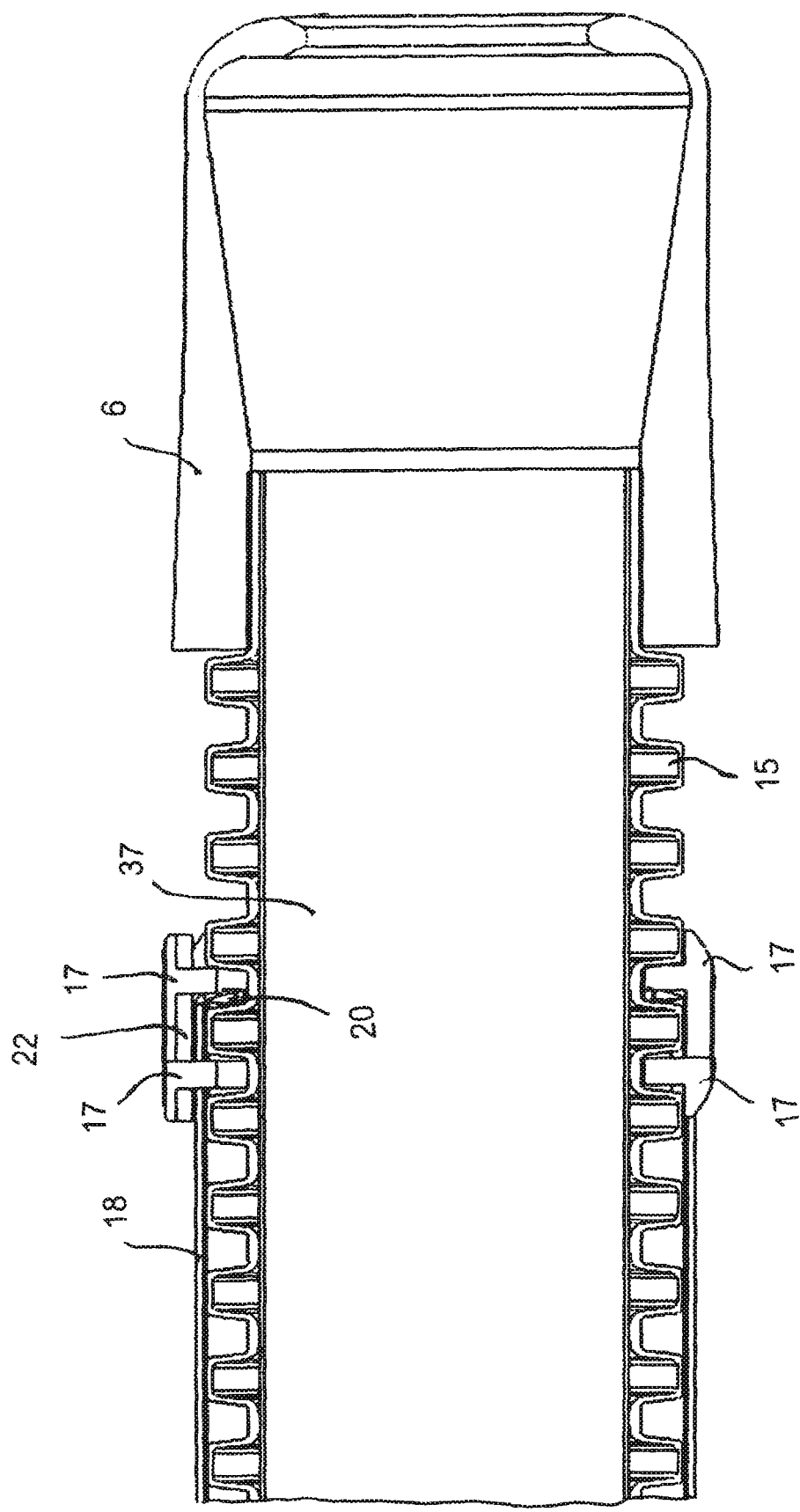
Figure 11C:
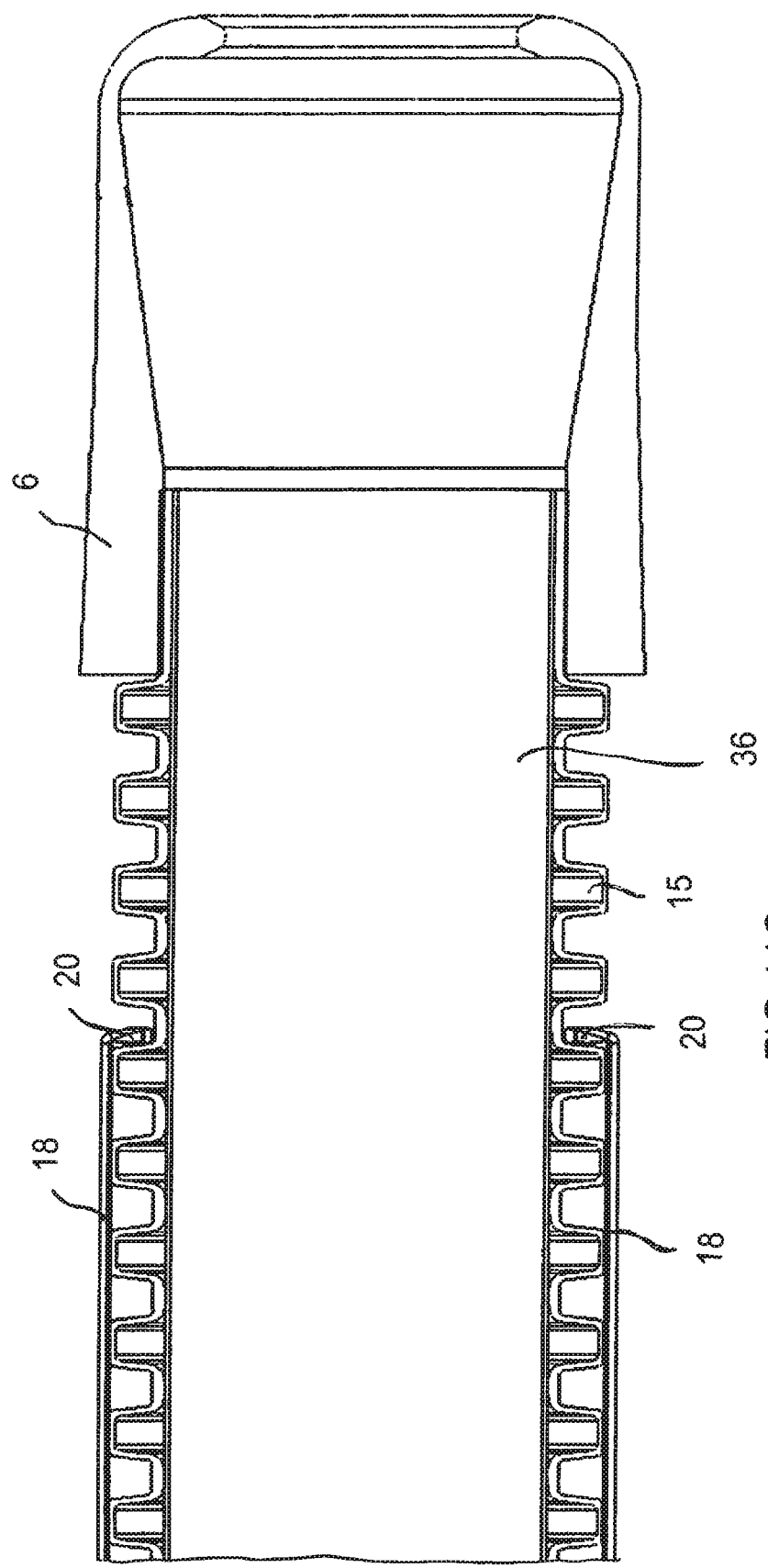

FIGS. 6 and 8 are perspective views of the entire insertion device 1 and FIG. 7 is a fragmentary side view of the proximal end and part of the working length of the insertion device, in which the outer jacket 5 has been removed. It can therefore be seen that the corrugated tube 15 extends distally beyond the strain relief retainer 7 to the tip 6 and that vertebrae 16 are clipped between several of the corrugations. Although only five vertebrae are shown in FIGS. 6 and 8, as many as twelve or more may be provided, depending on the working length and the application for which the insertion device is intended. The vertebrae may have slits formed radially therein to aid in slipping them over the corrugated tube. The last vertebra in the distal direction is a locking ring or termination vertebra 17. Whereas FIGS. 6 and 7 show the insertion device in the unlocked condition, FIG. 8 shows it in the locked condition, which will be discussed in more detail below. FIGS. 6, 7 and 8 also show staples or tendons 18 extended axially along the outer periphery of the corrugated tube 15.

Figure 12:
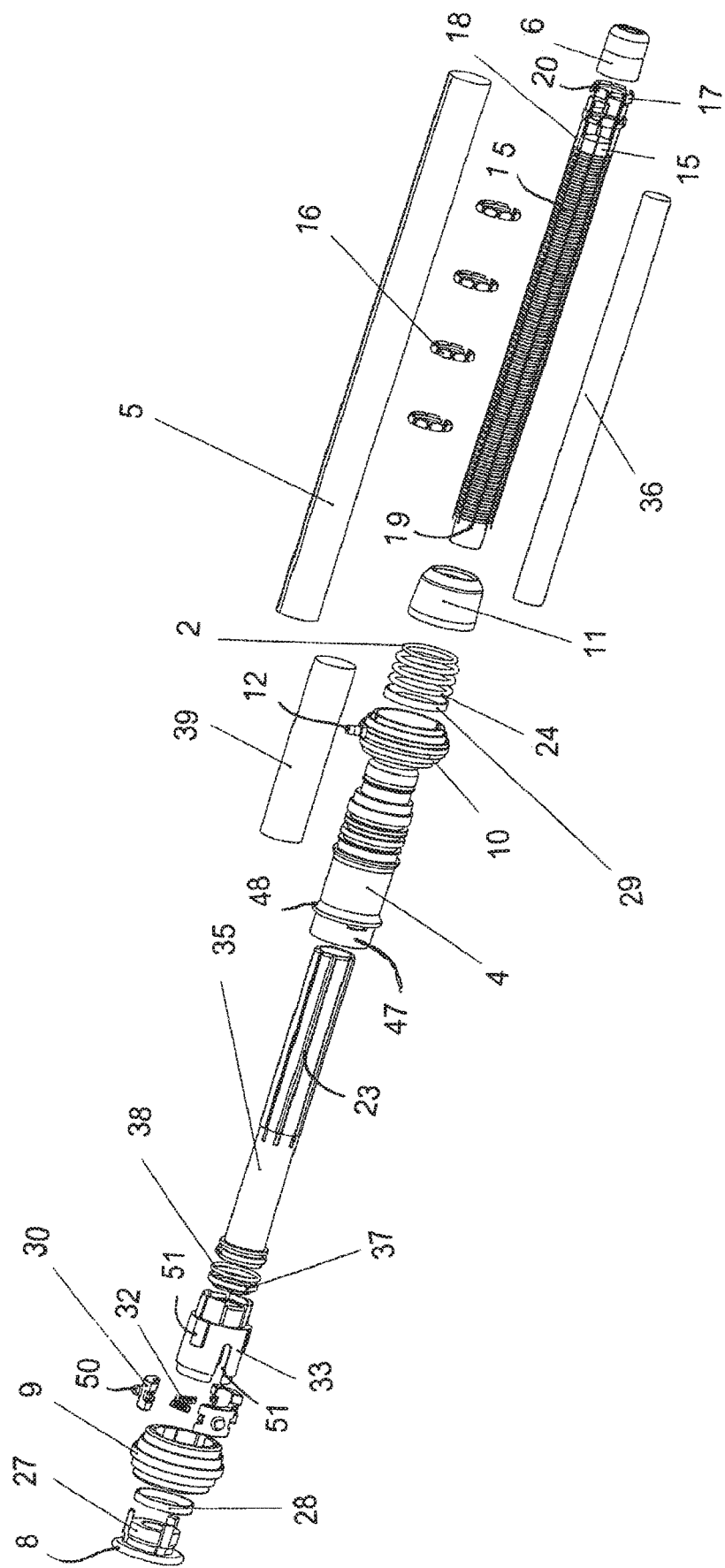
FIG. 12 is an exploded, perspective view of the insertion device.

As is seen in the fragmentary side, perspective and longitudinal-sectional views of FIGS. 9A and 9B, 10A and 10B and 11A, 11B and 11C, the tendons or staples 18 are looped through holes or slits 22 in the vertebrae 16 and the locking ring 17. The locking rings 17 have been omitted in FIGS. 9B and 10B to show details of the tendons or staples 18. The tendons or staples 18 have ends 19 extending proximally, as shown in FIG. 12. The tendons or staples 18 may be fixedly connected to the locking ring 17, such as by adhesive, weldments or solder joints. However, FIGS. 9B and 11A, 11B and 11C show that the tendons or staples 18 have a U-shape with legs passing through the holes 22 in the vertebrae 16 and cross pieces 20 disposed just distally beyond the locking ring 17. It can be seen particularly clearly in FIG. 11A that the cross pieces 20 of the tendons or staples 18 are captured and prevented from migrating distally by two locking rings 17 between which the cross pieces H are sandwiched in a valley or trough between two peaks or crests of the corrugated tube 15.

The number and location of the tendons or staples 18 and the vertebrae 16 axially and circumferentially may be chosen in such a way as to vary the stiffness of the insertion device 1 in zones. For example, more tendons or staples 18 and/or more vertebrae 16 may be placed in one zone along the working length than in another zone. The zone with more tendons or staples and/or vertebrae will be stiffer. Additionally, some of the tendons or staples may not extend over the entire working length and some may be fixed to vertebrae along the working length, all of which also varies stiffness in zones. As the insertion device flexes, some of the tendons or staples which are not fixed to particular vertebrae slide in the holes or slits 22.

Figure 13:
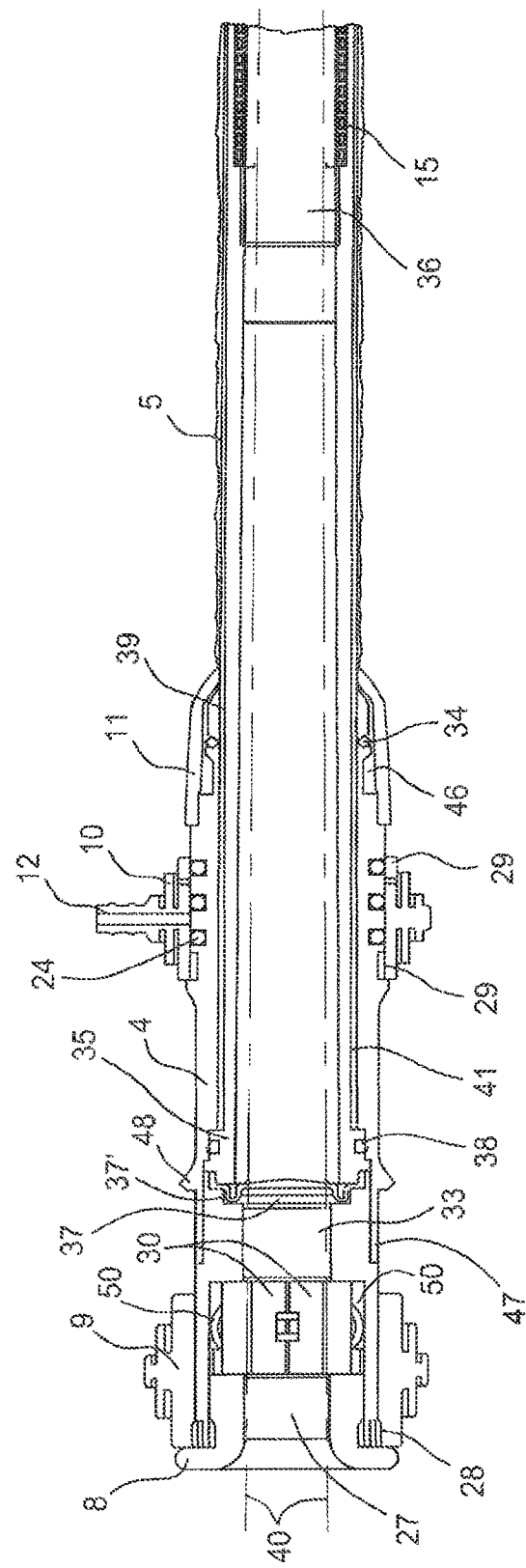
FIG. 13 is a fragmentary, longitudinal-sectional view of the proximal end and part of the working length of the insertion device.

The exploded view of FIG. 12 and the assembled sectional view of FIG. 13 show the end cap 8 at the proximal end, which surrounds a rear bushing 16. It may be seen that a marker band 28 is disposed between the actuator or bobbin 9 and the end cap 8. A clamping plate 30, which is also disposed within the actuator or bobbin 9, has three partial-plates 31a, 31b, 31c between which three springs 32 are disposed. A body tube 33, having slots 51, is disposed distally of the clamping plate 30.

A coupler 35, having grooves 23 extended axially on the periphery thereof, carries a septum seal 37 and an O-ring 38 provides a seal between the coupler 35 and the handle 4, which is slid over the coupler 35. Other marker bands 29 are disposed between the handle 4 and the sliding valve or slider 10 and the forward stop 11 is disposed over the distal end of the handle 4. O-rings 24 provide a seal between the slider 10 and the handle 4. An O-ring 34 is disposed between the forward stop 11 and the handle 4. It may also be seen that a heat shrink tubing 39 covers the coupler 35 and an inner liner or sleeve 36 is disposed within the corrugated tube 15. Moving distally, the corrugated tube 15 carrying the vertebrae 16, the tendons or staples 18, the locking ring 17 and the distal tip 6, is shown as well.

The inner sleeve 36 provides a surface over which the instrument 40 will pass smoothly within the corrugated tube 15. The corrugated tube 15 may be formed of nylon or another suitable material. The inner sleeve 36 may be made from a sheet of polyester film, which has an adhesive coating on one side. The inner sleeve 36 is rolled around an inflatable mandrel and heated in an oven, to form a bonded seam and is sealed to an inner surface of the corrugated tube 15. The corrugations of the corrugated tube 15 have peaks and valleys, as mentioned above. As viewed from within the corrugated tube 15, the inner sleeve 36 adheres to the peaks and extends somewhat into the valleys of the corrugations as dimples. Therefore, as the insertion device bends, the inner sleeve 36 stays tight along the corrugations on the outside of the bend and crinkles at the inside of the bend. The peaks and valleys of the corrugations also need not be of equal length along the length of the corrugated tube 15. For example, 70% of the length may be peaks and 30% valleys or 80% of the length may be peaks and 20% valleys. These variations will add to the adhesion of the inner sleeve 36 to the corrugated tube 15 and reduce the formation of dimples. However, a 50/50 corrugation ratio is shown in the figures.

The outer jacket 5 may be formed of polyurethane or another suitable material which is similarly a flat sheet that is rolled and seamed. The outer jacket 5 extends to the distal tip 6 and the inner sleeve 36 terminates with the end of the corrugated tube 15, the ends of which are "cuffed" to allow attachment of components.

Figure 14:
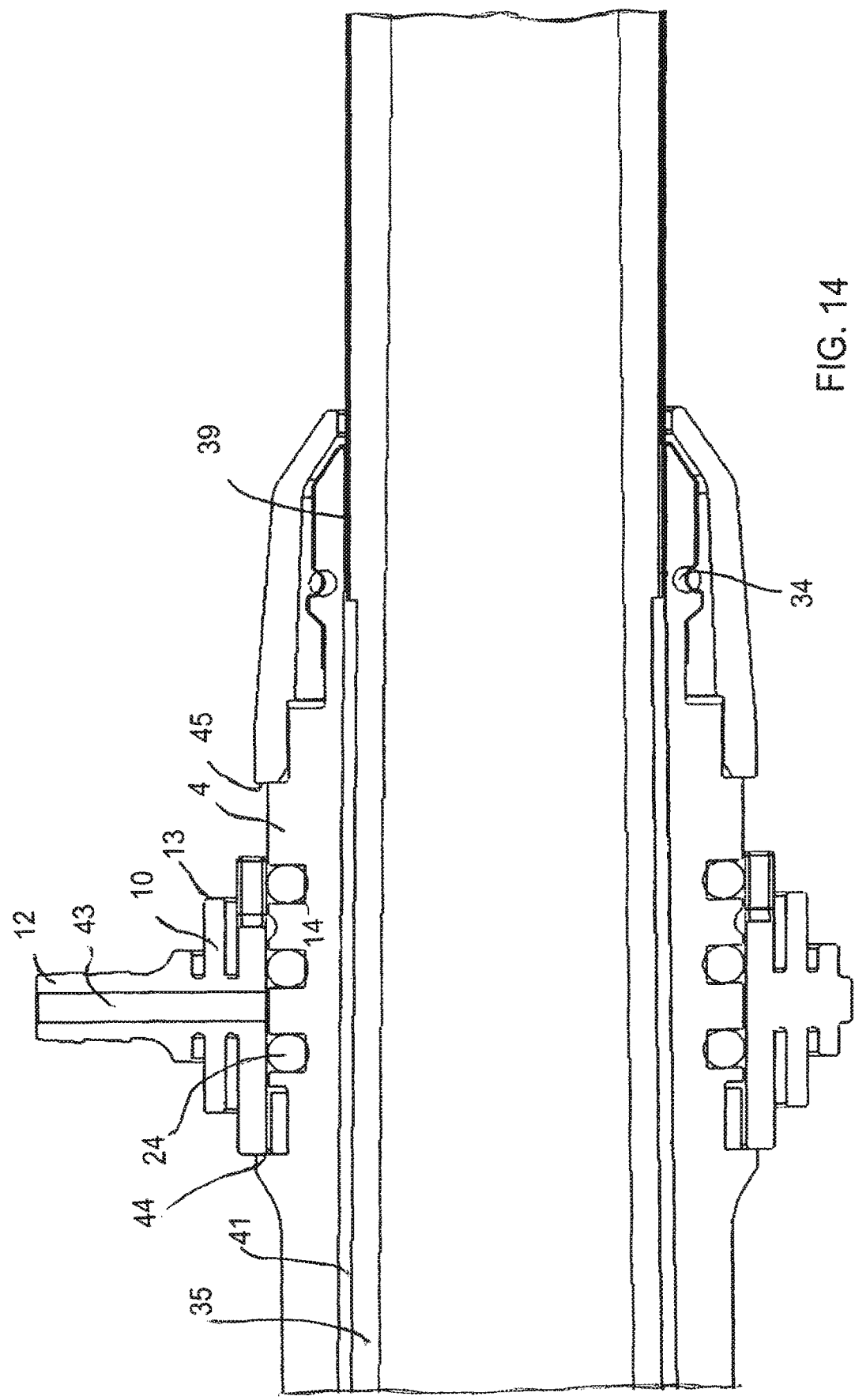
FIG. 14 is a greatly enlarged, fragmentary, side-longitudinal-sectional view of a proximal section of the insertion device.
Figure 15:
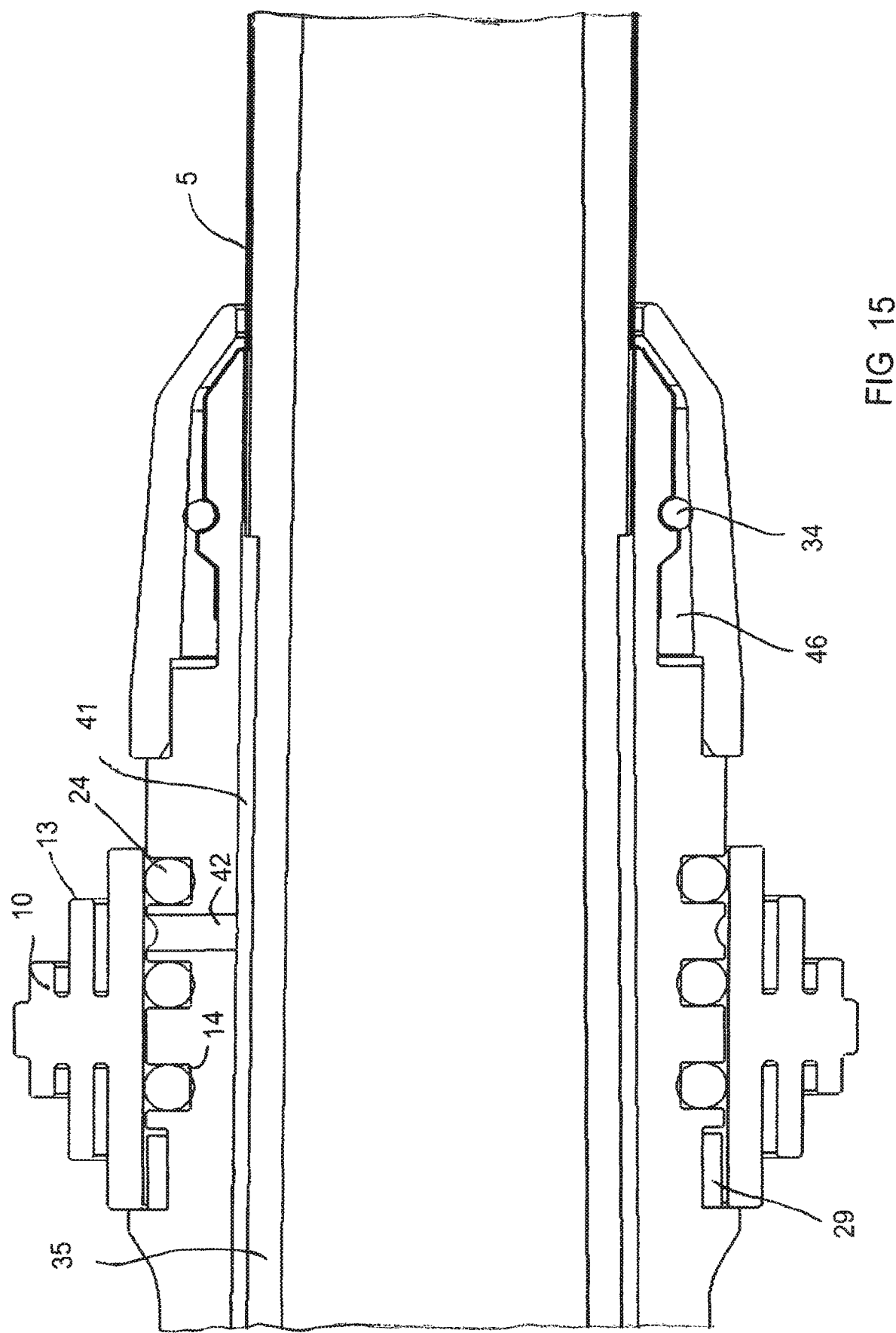
FIG. 15 is a fragmentary, top-longitudinal-sectional view of the proximal section of the insertion device.

The sectional views of FIGS. 14 and 15 show greater detail of the construction of the slider or sliding valve 10 having the nipple 12. The slider 10, which encircles the handle 4, has a sliding so-called tire valve thumb grip 13 and is sealed thereto by the O-rings 24 which are disposed in recesses 14 in the handle 4.

It may be seen that the handle 4 and the coupler 35 define an annular vacuum plenum volume 41 therebetween which extends in longitudinal direction of the handle 4. The O-ring 2 provides a seal at the proximal end of the volume 41. A vacuum inlet/outlet hole or port 42 is formed in the body of the handle 4 and communicates with the volume 41. The sliding valve or slider 10 also has a vacuum inlet/outlet 43 for the connection or nipple 12. When the slider 10 is slid toward an annular stop 44, the vacuum inlet/outlet 43 is not in alignment with the vacuum inlet/outlet hole 42. However, when the slider 10 is slid toward an annular stop 45, the vacuum inlet/outlet 43 and the vacuum inlet/outlet hole 42 are aligned, providing communication between the connection or nipple 12 and the volume 41. Therefore, during operation, the slider 10 is slid toward the stop 45 to apply vacuum to stiffen the hollow body. The slider 10 is slid toward the stop 44 to vent the vacuum to atmospheric pressure making the hollow body flexible again.

When vacuum is applied to the volume 41 in the manner described above, the outer jacket 5 and the corrugated tube 15 approach each other with the staples or tendons 18 sandwiched and frictionally locked therebetween. Therefore, the vacuum connection or nipple 12 acts as a device for transitioning the hollow body 4, 6, 35, 5, 36, between a relatively flexible condition and a relatively stiff condition through the application of a vacuum. As long as the vacuum is applied, the insertion device 1 maintains it condition, whether flexed or straight. When it is desired to resume flexibility of the insertion device 1, the vacuum is vented or replaced by air at ambient or positive pressure. This causes the corrugated tube 15 and the outer jacket 5 to release the tendons or staples 18 and the corrugated tube 15 and allows the inherent stiffness of the corrugated tube 15 to place the insertion device 1 into its normally flexible condition.

The tendons, staples or wires 18 are passive elements which are not in tension at any time. The tendons or staples float within the hollow body 4, 6, 35, 5, 36, 15 when it is in the flexible condition, except where they are fixed to the locking rings 17. The tendons or staples are frictionally locked by the corrugated tube 15 and the outer jacket or sleeve 5 when the hollow body is in the stiff condition. However, in both the relatively flexible condition and the relatively stiff condition, the tendons or staples have no active control imposed on them and are not pulled or constrained.

Figure 16:
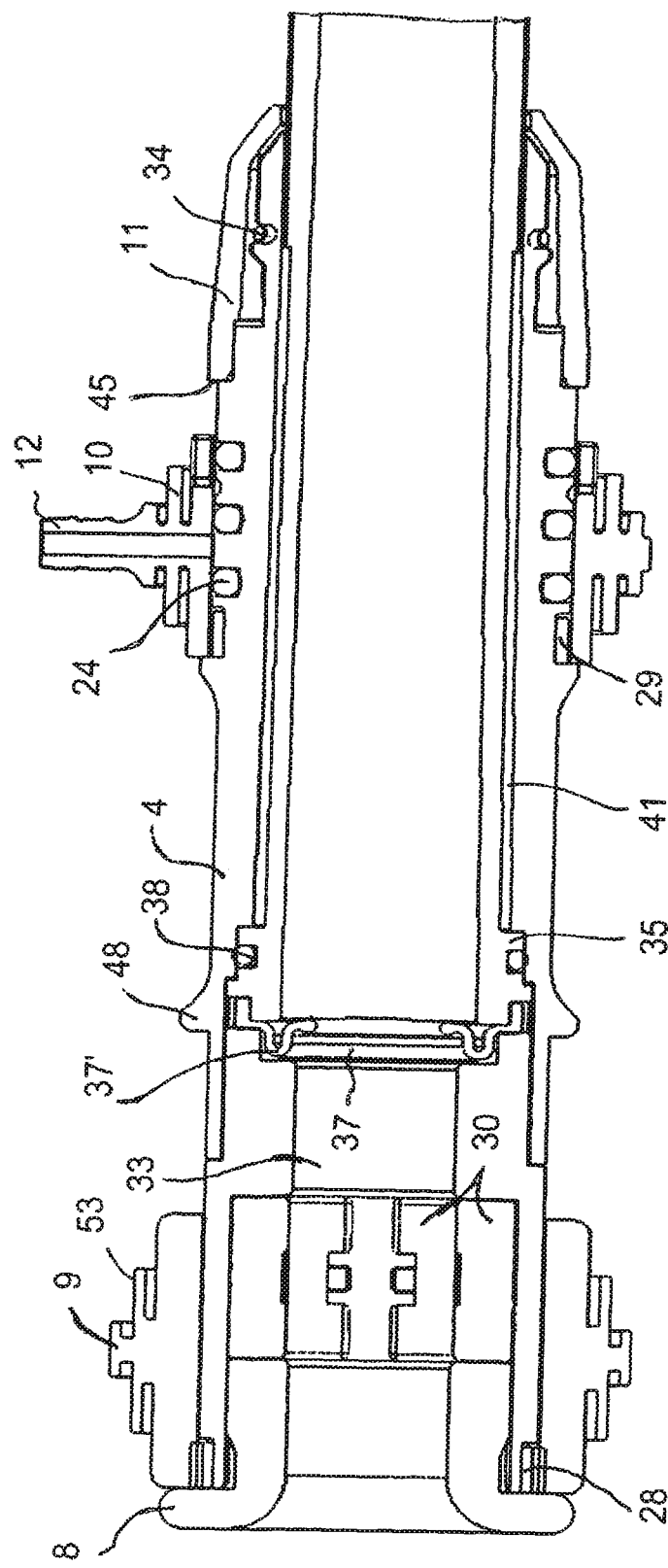
FIG. 16 is a fragmentary, side-longitudinal-sectional view of the proximal end of the insertion device.

As mentioned above, a comparison between FIGS. 6 and 8 reveals that the actuator or bobbin 9 in FIG. 6 is adjacent the end cap 8 in a non-actuated condition, while in FIG. 8 the actuator or bobbin 9 is in an actuated condition, in which it has been moved over an extension 47 of the handle 4 and against a collar 48 of the handle 4. FIGS. 16 and 18 also show the actuator or bobbin 9 in the non-actuated condition, whereas FIG. 17 shows the actuator or bobbin in the actuated condition, but in greater detail.

As is seen in FIGS. 12-13, 16-18 and 19A, 19B and 19C, the three partial-plates or partial-shells 31a, 31b, 31c of the clamping plate 30 have detents 50 protruding therefrom. FIGS. 17, 18 and 19A, 19B and 19C in particular show that the springs 32 bias the partial-plates and therefore the detents 50 through slots 51 in the body tube 33 and into corresponding recesses 52 in the inner peripheral surface of the actuator or bobbin 9 in the non-actuated condition. When a sliding, so-called tire valve thumb grip 53 of the actuator or bobbin 9 is pushed by the operator of the device and the actuator or bobbin is slid distally toward the collar 48 of the handle 4, the detents 50 slide out of the recesses 52 against the force of the springs 32. This causes the partial-plates 31a, 31b, 31c to move toward each other radially and against the instrument 40, such as an endoscope or a colonoscope represented by a dot-dash line in FIG. 13, for holding the instrument in place. When the actuator or bobbin 9 is slid proximally, the detents 50 once again fall into the recesses 52 due to the force of the springs 32, so that the partial-plates 31a, 31b, 31c move radially outwardly and release the instrument 40. Therefore, the actuator or bobbin 9 and the clamping plate 30 form a locking and unlocking device to be activated by the operator for locking the handle 4 to and unlocking the handle 4 from the instrument 40.

Figure 17:
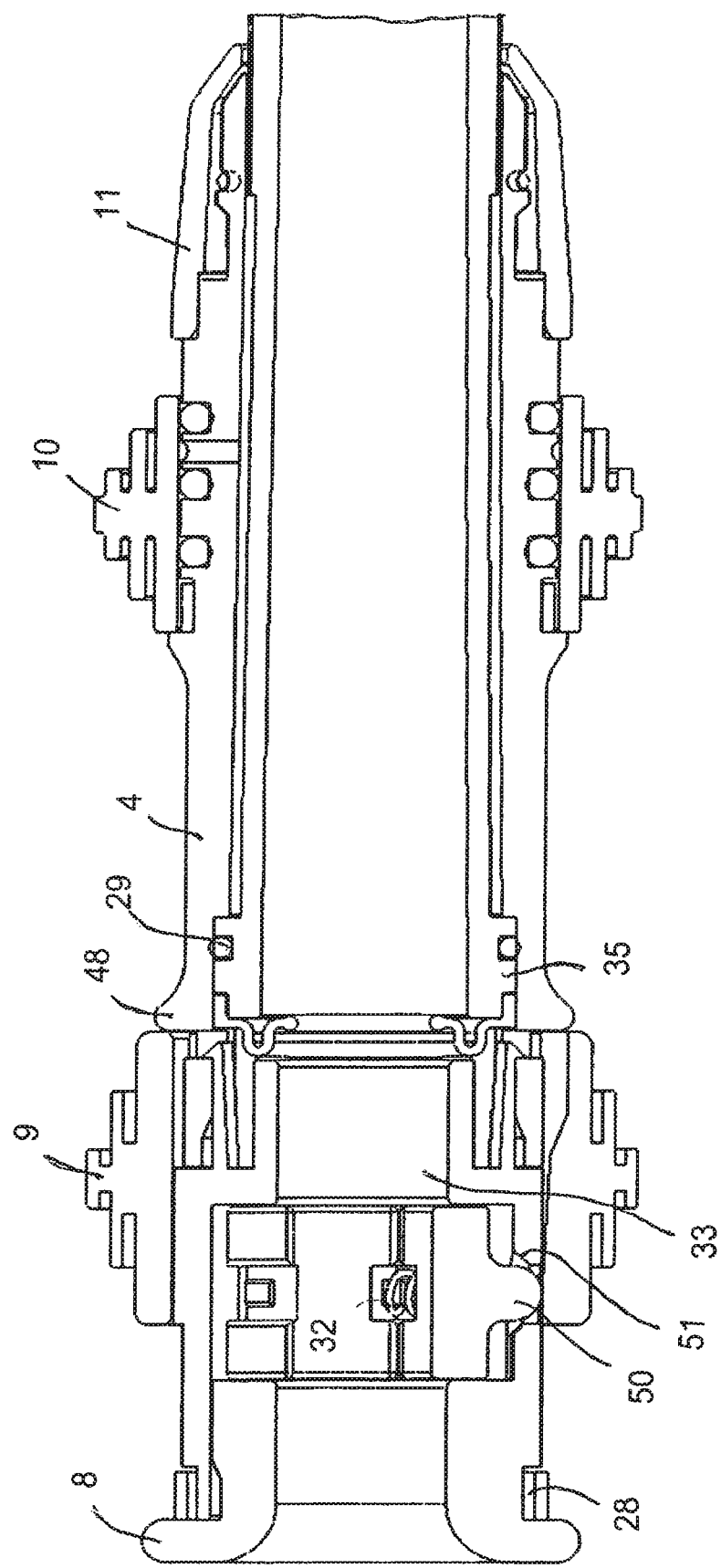
FIG. 17 is a fragmentary, top-longitudinal-sectional view of the proximal end of the insertion device in the actuated condition.
Figure 18:
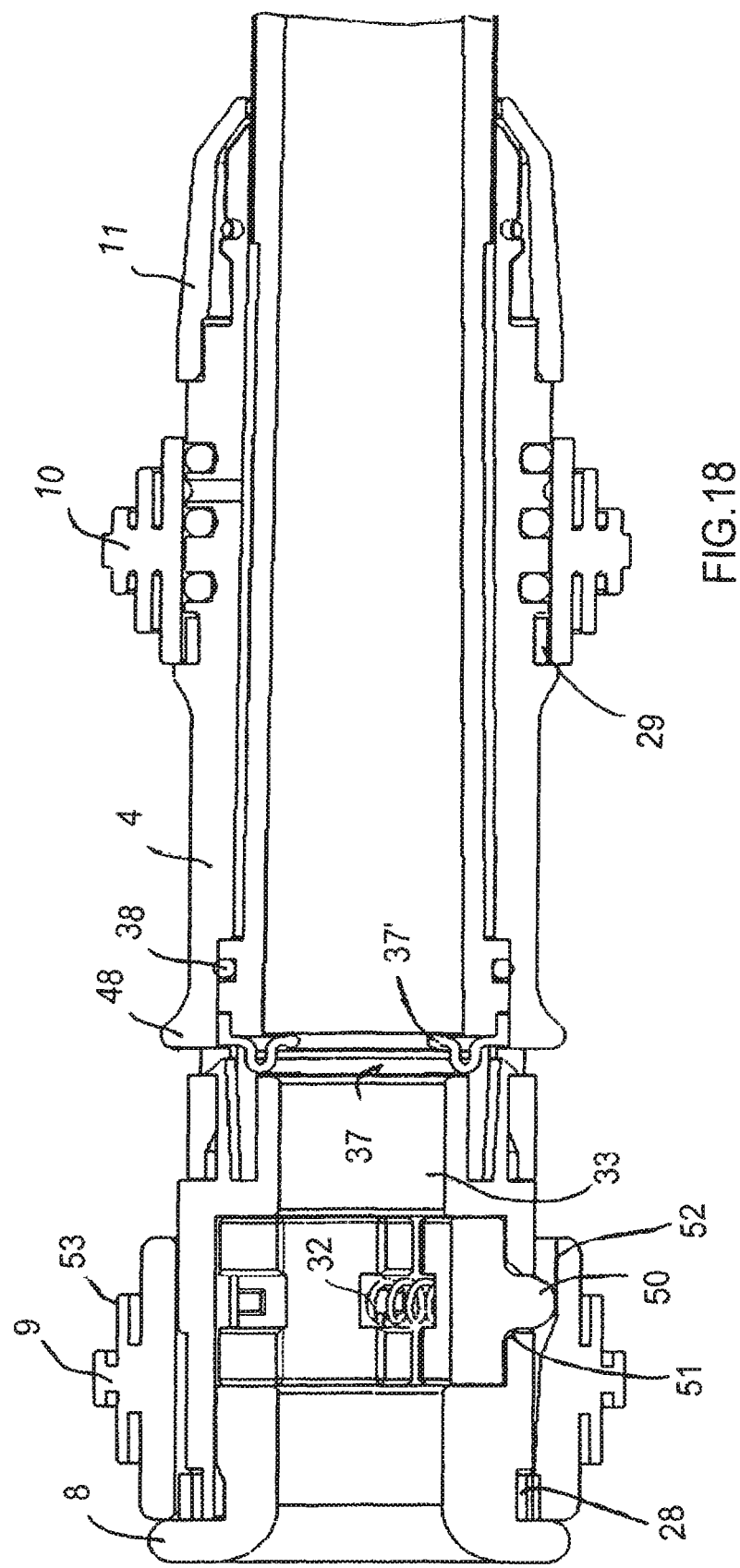
FIG. 18 is a fragmentary, top-longitudinal-sectional view of the proximal end of the insertion device similar to FIG. 17, in a non-actuated condition.

FIGS. 16, 17 and 18 also show the septum seal or valve assembly 37 in greater detail, as well as the end cap 8 which is inserted into the proximal end of the handle 1. End caps 8 with various sized openings may be used in dependence on the instrument being used. The instrument passes through the hollow body and emerges at the distal tip 6. It may be seen that the septum seal or septum valve assembly 37 has a diaphragm 37' resting in a recess in the coupler 35.

Figure 19B:
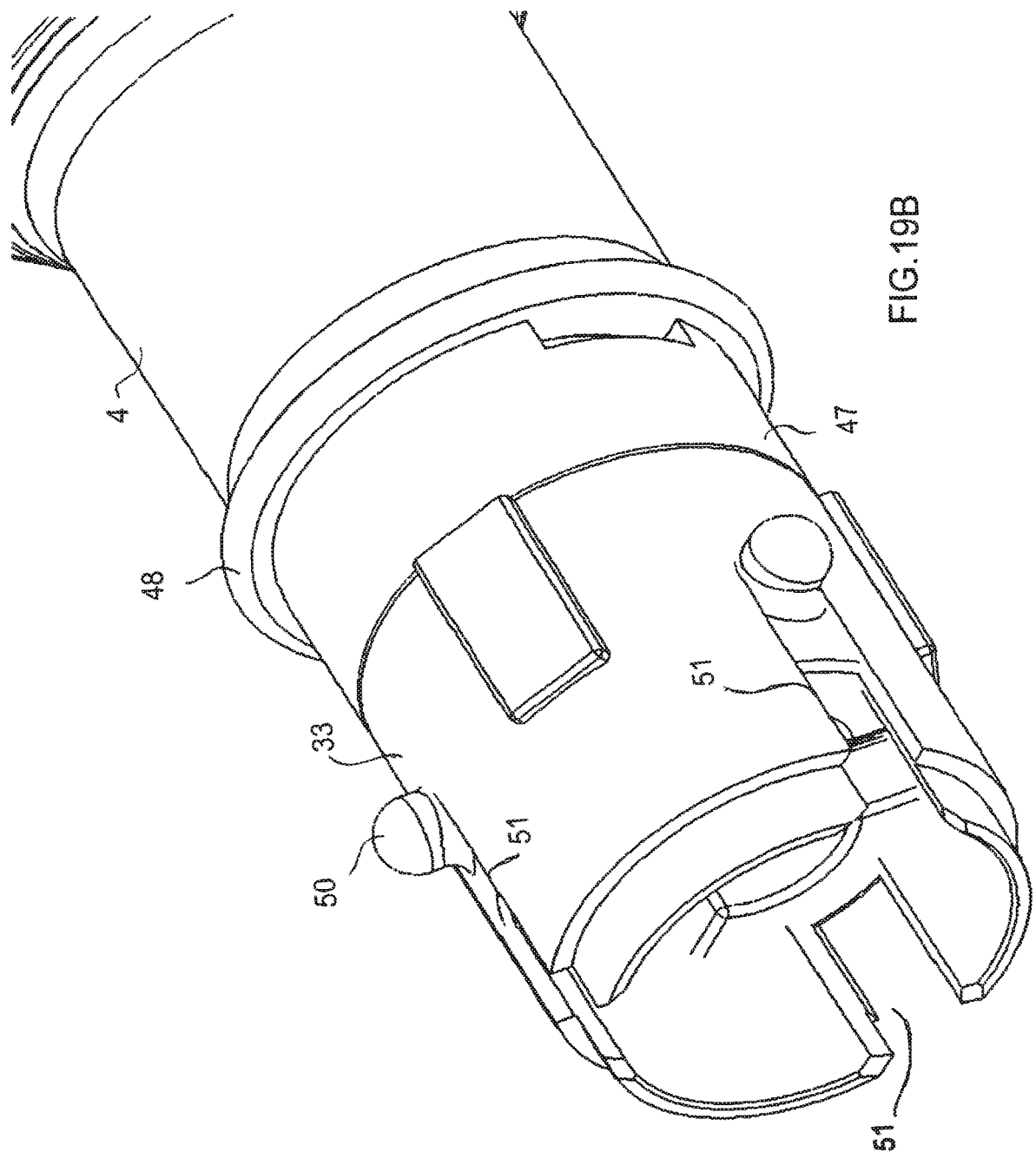
Figure 19C:
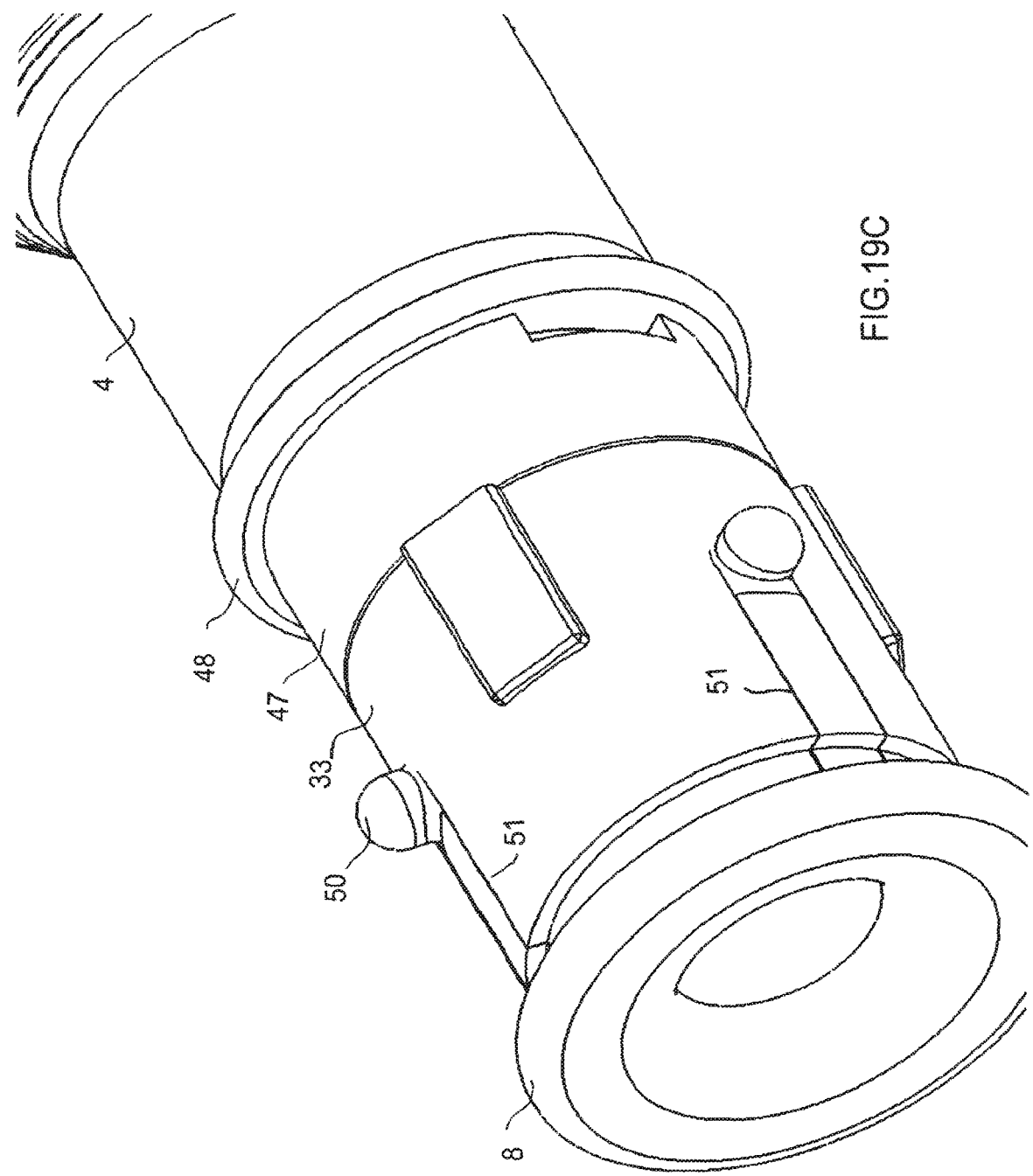

A comparison of FIGS. 19A, 19B, 19C and 19D also shows that in FIG. 19A merely the handle 4 with the extension 47 and the collar 48 as well as the partial-plates 31a, 31b, 31c are shown, while the body tube 33 has been slid over the partial-plates in FIG. 19B, the end cap 8 has been added at the proximal end in FIG. 19C and the actuator or bobbin 9 has been added distally of the end cap in FIG. 19D.

The insertion device is intended to be used in a manner similar to prior art devices. Therefore, the insertion device will be placed over the endoscope. The endoscope will then be inserted into the rectum. The insertion device will then be pushed in its flexible condition, to follow the curvature of the scope. The insertion device will then be stiffened, allowing the scope to be pushed forward with less pressure exerted on the colon of the patient. This procedure can be repeated until the scope reaches the cecum.

An alternative use of the insertion device is to aid in small bowel endoscopy. The insertion device is placed over the endoscope. The endoscope is inserted into the patient transorally, through the stomach and then partially into the small bowel. The insertion device is then pushed in its flexible condition, to follow the curvature of the scope. The insertion device is then stiffened, allowing the scope to be pushed forward without the scope looping in the stomach.

Another use of the insertion device is for aiding in access to internal body parts, such as the gallbladder, through an opening of an internal body cavity, such as the stomach. The insertion device is placed over the endoscope. The endoscope is inserted into the patient transorally, through the stomach and then up against the internal surface of the stomach. The insertion device is then pushed in its flexible condition, to follow the curvature of the scope. The insertion device is then stiffened, allowing the surgeon to create an opening in the stomach wall without the scope looping in the stomach. Once the opening is created, the insertion device and the scope can be advanced outside the stomach. The insertion device can then be stiffened to create a stable platform to perform surgical procedures outside of the stomach. The insertion device could contain one or more features (i.e. balloons) for sealing the outer periphery of the insertion device to the stomach wall to prevent gastric fluids from exiting the stomach.

It is noted that various individual features of the inventive processes and systems may be described only in one exemplary embodiment herein. The particular choice for description herein with regard to a single exemplary embodiment is not to be taken as a limitation that the particular feature is only applicable to the embodiment in which it is described. All features described herein are equally applicable to, additive, or interchangeable with any or all of the other exemplary embodiments described herein and in any combination or grouping or arrangement. In particular, use of a single reference numeral herein to illustrate, define, or describe a particular feature does not mean that the feature cannot be associated or equated to another feature in another drawing figure or description. Further, where two or more reference numerals are used in the figures or in the drawings, this should not be construed as being limited to only those embodiments or features, they are equally applicable to similar features or not a reference numeral is used or another reference numeral is omitted.

The foregoing description and accompanying drawings illustrate the principles, exemplary embodiments, and modes of operation of the systems, apparatuses, and methods. However, the systems, apparatuses, and methods should not be construed as being limited to the particular embodiments discussed above. Additional variations of the embodiments discussed above will be appreciated by those skilled in the art and the above-described embodiments should be regarded as illustrative rather than restrictive. Accordingly, it should be appreciated that variations to those embodiments can be made by those skilled in the art without departing from the scope of the systems, apparatuses, and methods as defined by the following claims.

What is claimed is:

1. A variably-flexible, locking insertion device, comprising:
    a hollow body having a proximal end with an entrance for receiving an instrument, a distal end with a tip for protrusion of the instrument, and a handle to be gripped by an operator;
    a negative pressure source;
    a vacuum-actuated transitioning device, comprising:
        a vacuum connection in fluidic communication with the hollow body and
        selectively connected to the negative pressure source to apply a negative pressure to the hollow body, to thereby transition the hollow body into a relatively stiff condition; and
        a release mechanism selectively disconnecting the negative pressure source from the vacuum connection to vent out from the hollow body an applied negative pressure, to thereby transition the hollow body into a relatively flexible condition; and
    tendons disposed within the hollow body for maintaining the hollow body in the relatively flexible and relatively stiff conditions, the tendons being neither in tension nor compression when the hollow body is in the relatively stiff condition.

2. The insertion device according to claim 1, which further comprises:
    a corrugated tube around the hollow body for transmitting torque from the proximal end toward the distal end; and
    an inner sleeve disposed within the corrugated tube for preventing vacuum leakage and aiding in insertion of the instrument.

3. The insertion device according to claim 2, wherein the tendons are disposed along the corrugated tube along the hollow body to maintain the hollow body in the relatively flexible and relatively stiff conditions.

4. The insertion device according to claim 3, which further comprises an outer jacket around the hollow body such that the tendons are at least partly disposed between the outer jacket and the corrugated tube, and the transitioning device applies a negative pressure between the outer jacket and the corrugated tube to fictionally lock the tendons in place.

5. The insertion device according to claim 1, which further comprises tendon guiding devices disposed circumferentially about the hollow body and shaped to maintain the tendons in a longitudinal orientation with respect to the hollow body.

6. The insertion device according to claim 5, wherein the tendon guiding devices are vertebrae disposed along the hollow body and having holes guiding the tendons.

7. The insertion device according to claim 6, wherein:
    the vertebrae include at least one last vertebra closest to the distal end; and
    each two of the tendons form legs of a U-shaped configuration passing through the holes and are interconnected by a crosspiece distally of the at least one last vertebra.

8. A variably-flexible, locking insertion device, comprising:
    a hollow body having a proximal end with an entrance for receiving an instrument, a distal end with a tip for protrusion of the instrument, and a handle to be gripped by an operator;
    a negative pressure source;
    a positive pressure source;
    a vacuum-actuated transitioning device comprising:
        a vacuum connection in fluidic communication with the hollow body and selectively connected to:
            the negative pressure source to apply a negative pressure to the hollow body, to thereby transition the hollow body into a relatively stiff condition; and
            the positive pressure source to apply a positive pressure to the hollow body, to thereby transition the hollow body from the relatively stiff condition to a relatively flexible condition; and
        a release mechanism selectively disconnecting and connecting the negative pressure source and the positive pressure source to the vacuum connection; and
    tendons disposed within the hollow body for maintaining the hollow body in the relatively flexible and relatively stiff conditions, the tendons being neither in tension nor compression when the hollow body is in the relatively stiff condition.

9. The insertion device according to claim 8, which further comprises:
    a corrugated tube around the hollow body for transmitting torque from the proximal end toward the distal end; and
    an inner sleeve disposed within the corrugated tube for preventing vacuum leakage and aiding in insertion of the instrument.

10. The insertion device according to claim 9, wherein the tendons are disposed along the corrugated tube along the hollow body to maintain the hollow body in the relatively flexible and relatively stiff conditions.

11. The insertion device according to claim 10, which further comprises an outer jacket around the hollow body such that the tendons are at least partly disposed between the outer jacket and the corrugated tube, and the transitioning device applies a negative pressure between the outer jacket and the corrugated tube to frictionally lock the tendons in place.

12. The insertion device according to claim 8, which further comprises tendon guiding devices disposed circumferentially about the hollow body and shaped to maintain the tendons in a longitudinal orientation with respect to the hollow body.

13. The insertion device according to claim 12, wherein the tendon guiding devices are vertebrae disposed along the hollow body and having holes guiding the tendons.

14. The insertion device according to claim 13, wherein:
    the vertebrae include at least one last vertebra closest to the distal end; and
    each two of the tendons form legs of a U-shaped configuration passing through the holes and are interconnected by a crosspiece distally of the at least one last vertebra.

15. A variably-flexible, locking insertion device, comprising:
- a hollow body having a proximal end with an entrance for receiving an instrument, a distal end with a tip for protrusion of the instrument, and a handle to be gripped by an operator;
- a negative pressure source;
- a vacuum-actuated device, comprising:
  - an outer jacket surrounding the hollow body and defining a vacuum plenum volume between the hollow body and the outer jacket;
  - a vacuum inlet/outlet hole fluidically connected to the vacuum plenum volume and
  - selectively connected to the negative pressure source and applying a negative pressure that compresses the vacuum plenum volume to thereby transition the hollow body into a relatively stiff condition; and
  - a release mechanism selectively disconnecting the negative pressure source from the vacuum inlet/outlet hole to vent out from the hollow body an applied negative pressure, to thereby transition the hollow body into a relatively flexible condition; and
- tendons at least partly disposed between the outer jacket and the hollow body for maintaining the hollow body in the relatively flexible and relatively stiff conditions, the tendons being neither in tension nor compression when the hollow body is in the relatively stiff condition.

16. The insertion device according to claim 15, which further comprises:
- a corrugated tube around the hollow body for transmitting torque from the proximal end toward the distal end; and
- an inner sleeve disposed within the corrugated tube for preventing vacuum leakage and aiding in insertion of the instrument.

17. The insertion device according to claim 16, wherein the tendons are disposed along the corrugated tube along the hollow body to maintain the hollow body in the relatively flexible and relatively stiff conditions.

18. The insertion device according to claim 17, wherein the vacuum-actuated device applies a negative pressure between the outer jacket and the corrugated tube to frictionally lock the tendons in place.

19. The insertion device according to claim 15, which further comprises tendon guiding devices disposed circumferentially about the hollow body and shaped to maintain the tendons in a longitudinal orientation with respect to the hollow body.

20. The insertion device according to claim 19, wherein the tendon guiding devices are vertebrae disposed along the hollow body and having holes guiding the tendons.

21. The insertion device according to claim 20, wherein:
- the vertebrae include at least one last vertebra closest to the distal end; and
- each two of the tendons form legs of a U-shaped configuration passing through the holes and are interconnected by a crosspiece distally of the at least one last vertebra.

22. A variably-flexible, locking insertion device, comprising:
- a hollow body having a proximal end with an entrance for receiving an instrument, a distal end with a tip for protrusion of the instrument, and a handle to be gripped by an operator;
- a negative pressure source;
- a vacuum-actuated device, comprising:
  - a vacuum connection in fluidic communication with the hollow body and
  - selectively connected to the negative pressure source to apply a negative pressure to the hollow body, thereby transition the hollow body into a relatively stiff condition; and
  - a release mechanism selectively disconnecting the negative pressure source from the vacuum connection to vent out from the hollow body an applied negative pressure, to thereby transition the hollow body into a relatively flexible condition; and
- a network of longitudinal support beams disposed within the hollow body for maintaining the hollow body in the relatively flexible and relatively stiff conditions, the support beams being neither in tension nor compression when the hollow body is in the relatively stiff condition.

23. The insertion device according to claim 22, wherein each of the longitudinal support beams has a proximal end and a distal end and is linear from the proximal end to the distal end.

24. The insertion device according to claim 22, which further comprises:
- a corrugated tube around the hollow body for transmitting torque from the proximal end toward the distal end; and
- an inner sleeve disposed within the corrugated tube for preventing vacuum leakage and aiding in insertion of the instrument.

25. The insertion device according to claim 24, wherein the support beams are disposed along the corrugated tube along the hollow body to maintain the hollow body in the relatively flexible and relatively stiff conditions.

26. The insertion device according to claim 25, which further comprises an outer jacket around the hollow body such that the support beams are at least partly disposed between the outer jacket and the corrugated tube, and the transitioning device applies a negative pressure between the outer jacket and the corrugated tube to frictionally lock the support beams in place.

27. The insertion device according to claim 22, which further comprises beam guiding devices disposed circumferentially about the hollow body and shaped to maintain the support beams in a longitudinal orientation with respect to the hollow body.

28. The insertion device according to claim 27, wherein the beam guiding devices are vertebrae disposed along the hollow body and having holes guiding the support beams.

29. The insertion device according to claim 28, wherein:
- the vertebrae include at least one last vertebra closest to the distal end; and
- each two of the support beams form legs of a U-shaped configuration passing through the holes and are interconnected by a crosspiece distally of the at least one last vertebra.

* * * * *